US006649370B1

United States Patent
Murdin et al.

(10) Patent No.: US 6,649,370 B1
(45) Date of Patent: Nov. 18, 2003

(54) CHLAMYDIA ANTIGENS AND CORRESPONDING DNA FRAGMENTS AND USES THEREOF

(75) Inventors: Andrew D. Murdin, Ontario (CA); Raymond P. Oomen, Ontario (CA); Pamela L. Dunn, Ontario (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/427,533

(22) Filed: Oct. 26, 1999

Related U.S. Application Data

(60) Provisional application No. 60/132,271, filed on May 3, 1999, and provisional application No. 60/106,046, filed on Oct. 28, 1998.

(51) Int. Cl.$^7$ ............... C12P 21/06; C12N 1/20; C12N 15/00; C12N 5/00; C07H 21/04

(52) U.S. Cl. ............... 435/69.1; 435/252.3; 435/320.1; 435/325; 536/23.7

(58) Field of Search ............... 424/263.1; 435/69.1, 435/257.6, 252.3, 320.1, 325; 536/23.7

(56) References Cited

U.S. PATENT DOCUMENTS

| 5,028,530 A | * | 7/1991 | Lai et al. |
| 5,302,527 A | * | 4/1994 | Birkett et al. |
| 5,725,863 A | * | 3/1998 | Daniels |

FOREIGN PATENT DOCUMENTS

| WO | WO 99/27105 | 6/1999 |

OTHER PUBLICATIONS

Plotkin et al (*Vaccines* W.B. Saunders Co. Philadelphia, p. 571), 1988.*
Kalman, et al., Nature Genetics, 21, 385–389 (1999).
Magee, et al., Infection and Immunity, 63:2, 516–521 (1995).
Landers, et al., Infection and Immunity, 59:10, 3774–3777 (1991).
Jackson, et al., Abstracts of the 36th ICAAC, 272 (1996).
Magee, et al. Regional Immunology, 5, 305–311 (1993).
Igletseme, et al., Regional Immunology, 5, 317–324 (1993).
Jones, et al., Vaccine, 13:8, 715–723 (1995).
Pal, et al., Infection and Immunity, 64:12, 5341–5348 (1996)
Hahn, et al., The Journal of the American Medical Association, 266:2, 225–230 (1991).
Allegra, et al., European Respiratory Journal, 7:2, 2165–2168 (1994).
Björnsson, et al., Scandinavian Journal of Infectious Diseases, 28:1, 63–69 (1996).
Hahn, The Journal of Family Practice, 41:4, 345–351 (1995).
Hahn, et al., Epidemiology Infection, 117:3, 513–517 (1996).
Hahn, et al., Annals of Allergy, Asthma, and Immunology, 80:1, 45–49 (1988).
Fong, et al., Journal of Clinical Microbiology, 35:1, 48–52 (1997).
Ramirez, et al., Annals of Internal Medicine, 125:12, 979–982 (1996).
Chiu, et al., Circulation, 96:7, 2144–2148 (1997).
Campbell, et al., The Journal of Infectious Diseases, 172:2, 585–588 (1995).
Kuo, et al., Arteriosclerosis and Thrombosis, 13:10, 1501–1504 (1993).
Kuo, et al. The Journal of Infectious Diseases, 167:4, 841–849 (1993).
Melnick, et al., The American Journal of Medicine, 95, 499–504 (1993).
Saikku, et al., Annals of Internal Medicine, 116:4, 273–278 (1992).
Grayston, et al., The Journal of Infectious Diseases, 168:5, 1231–1235 (1993).
Campos, et al., Investigative Opthhalmology & Visual Science, 36:8, 1477–1491 (1995).
Grayston, et al., The Journal of Infectious Diseases, 161:4, 618–625 (1990).
Marrie, Clinical Infectious Diseases, 18:4, 501–515 (1994).
Wang et al., Chlamydial Infections, 329–333 (1986).
Saikku, et al., The Lancet, 2:8618, 983–985 (1988).
Thom, et al., The Journal of the American Medical Association, 268:1, 68–72 (1992).
Linnanmäki, et al., Circulation, 87:4, 1130–1134 (1993).
Bachmaier, et al., Science, 283, 1335–1339 (1999).
Iijima, et al., Journal of Clinical Microbiology, 32:3, 583–588 (1994).
Campbell, et al., Journal of Clinical Microbiology, 28:6, 1261–1264 (1990).
Melgosa, et al., FEMS Microbiology Letters, 112:2, 199–204 (1993).
Watson, et al., Microbiology, 141, 2489–2497 (1995).
Watson, et al., Nucleic Acids Research, 18:7, 5299 (1990).
Melgosa, et al., Infection and Immunity, 62:3, 880–886 (1994).
Takase, et al., Journal of Bacteriology, 169:12, 5692–5699 (1987).
Cagnon, et al., Protein Engineering, 4:7, 843–847 (1991).

(List continued on next page.)

Primary Examiner—Mark Navarro
(74) Attorney, Agent, or Firm—Ivor R. Elrifi; Nicholas P. Triano, III; Mintz, Levin, Cohn, Ferris, Glovsky and Popeo, P.C.

(57) ABSTRACT

In summary of this disclosure, the present invention provides a method of nucleic acid, including DNA, immunization of a host, including humans, against disease caused by infection by a strain of Chlamydia, specifically *C. pneumoniae*, employing a vector, containing a nucleotide sequence encoding an 98 kDa outer membrane protein of a strain of *Chlamydia pneumoniae* and a promoter to effect expression of the 98 kDa outer membrane protein gene in the host. Modifications are possible within the scope of this invention.

10 Claims, 23 Drawing Sheets

OTHER PUBLICATIONS

Figure 2A:
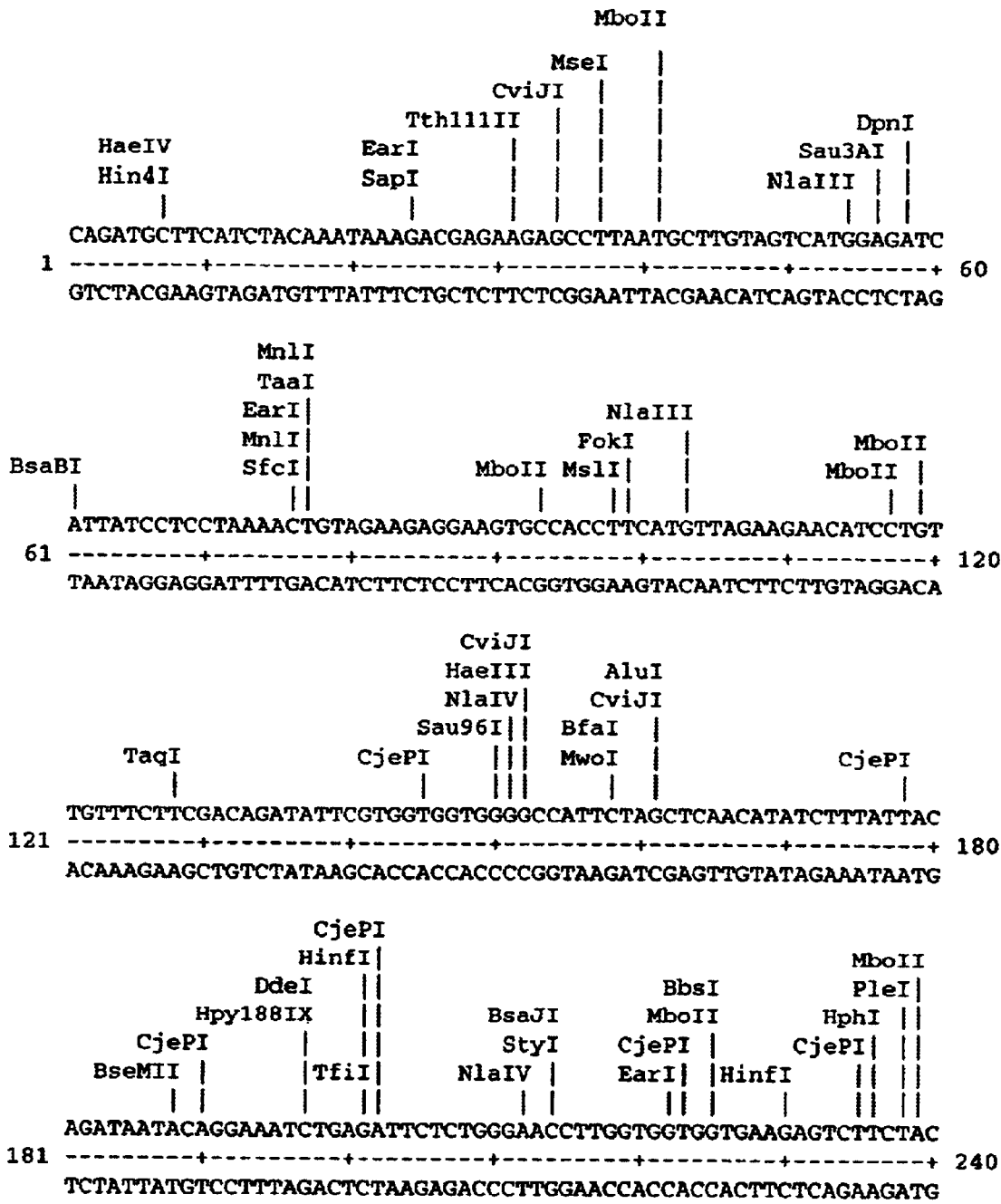
Figure 2F:
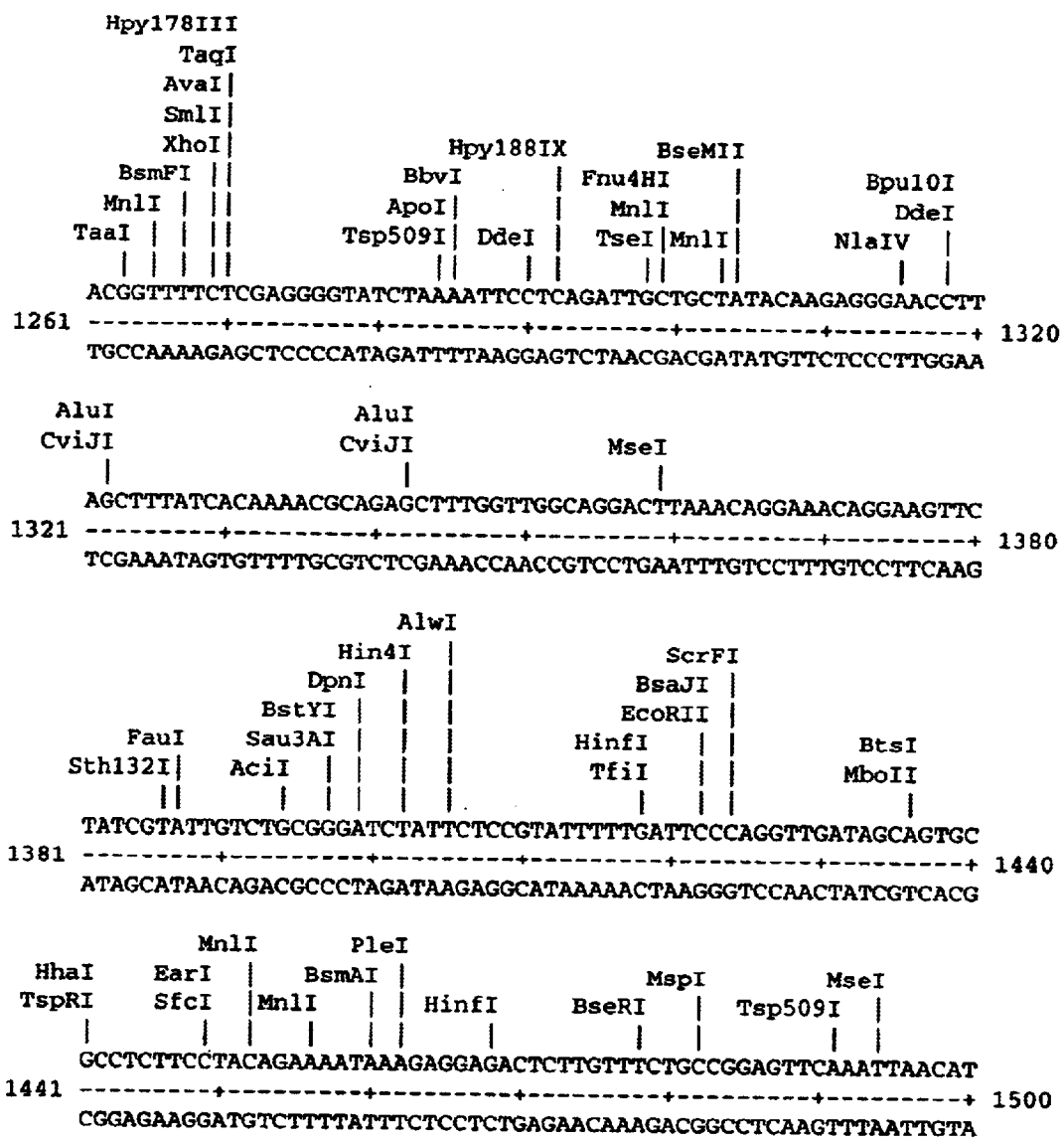
Figure 2I:
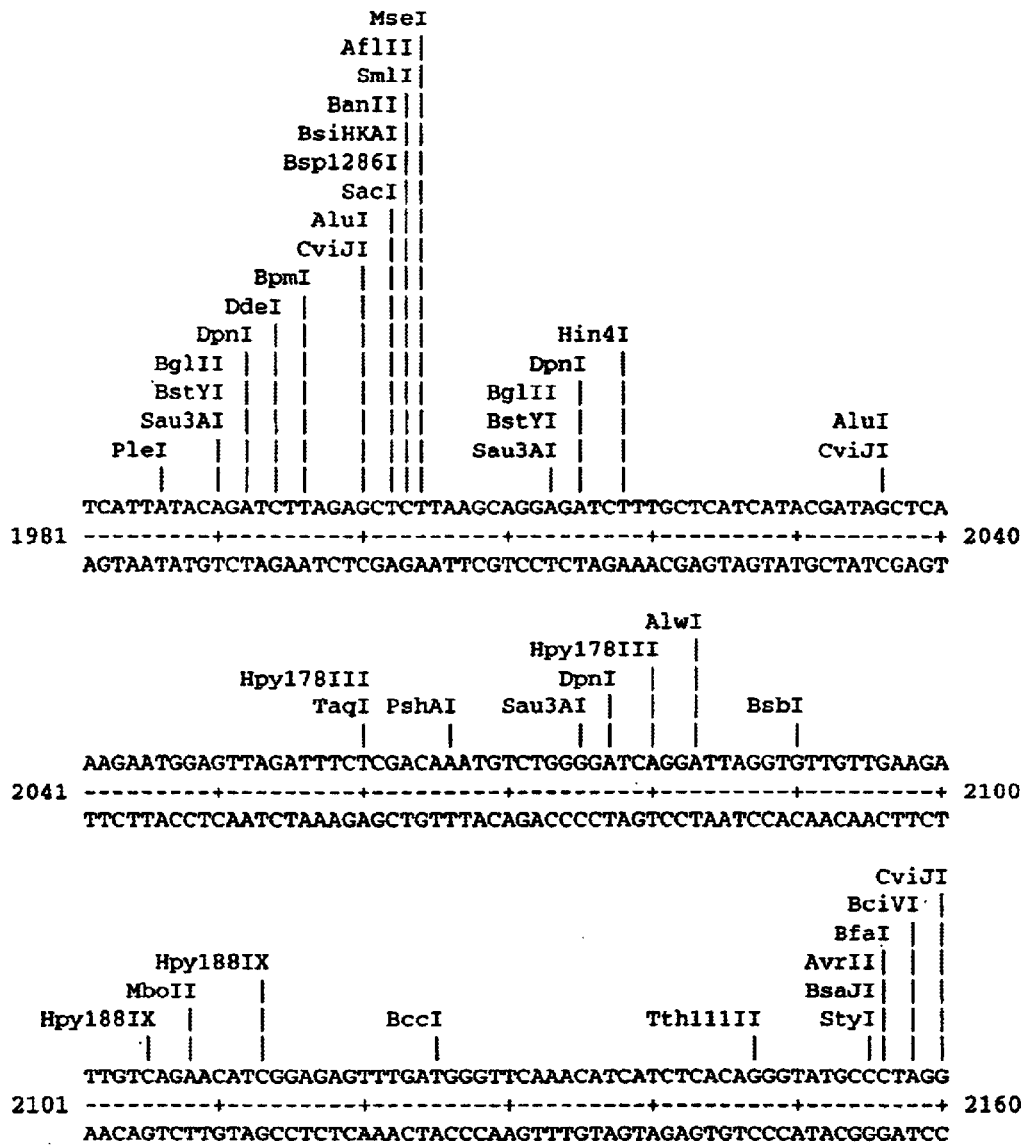
Figure 3A:
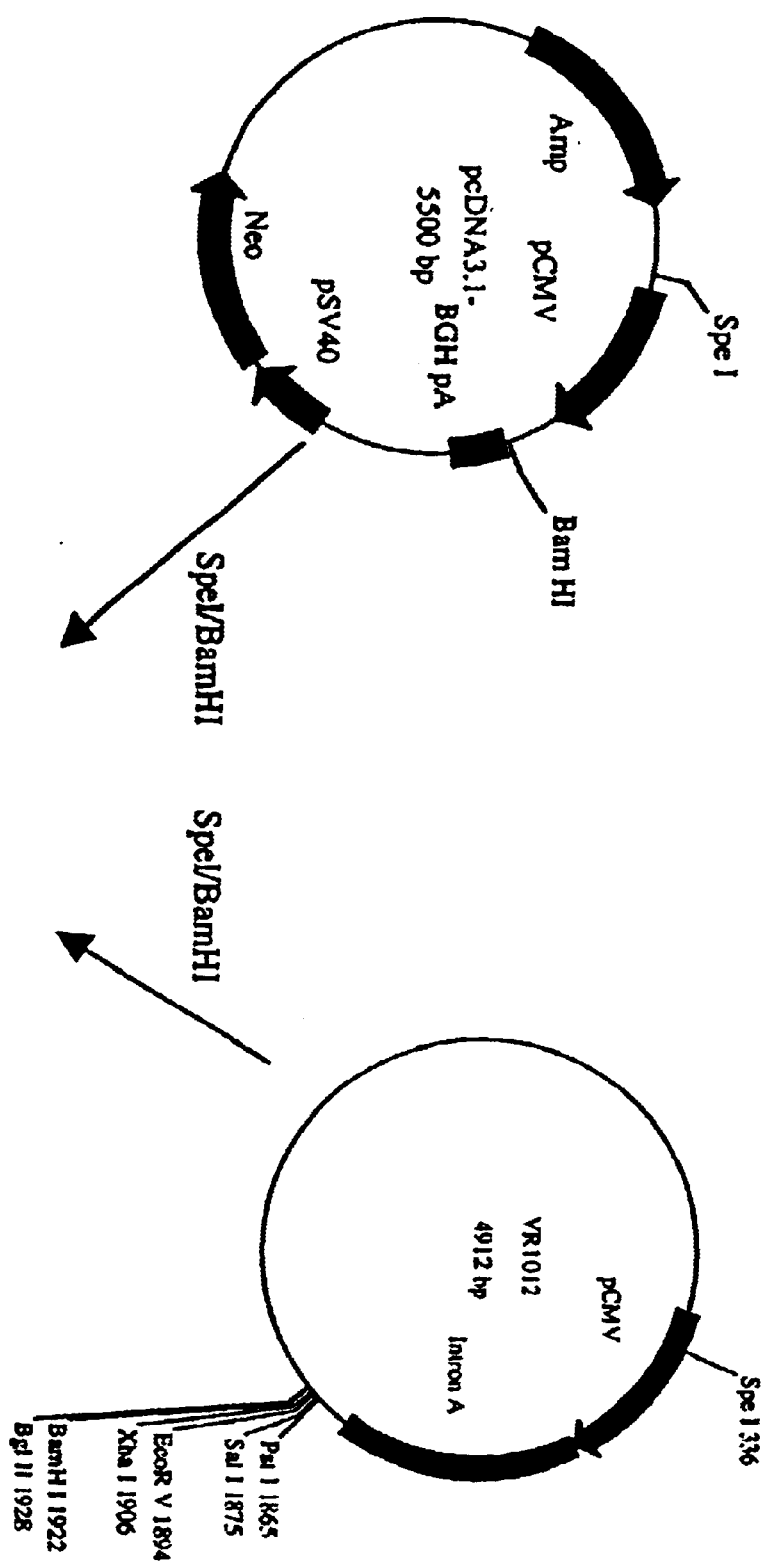
Figure 3B:
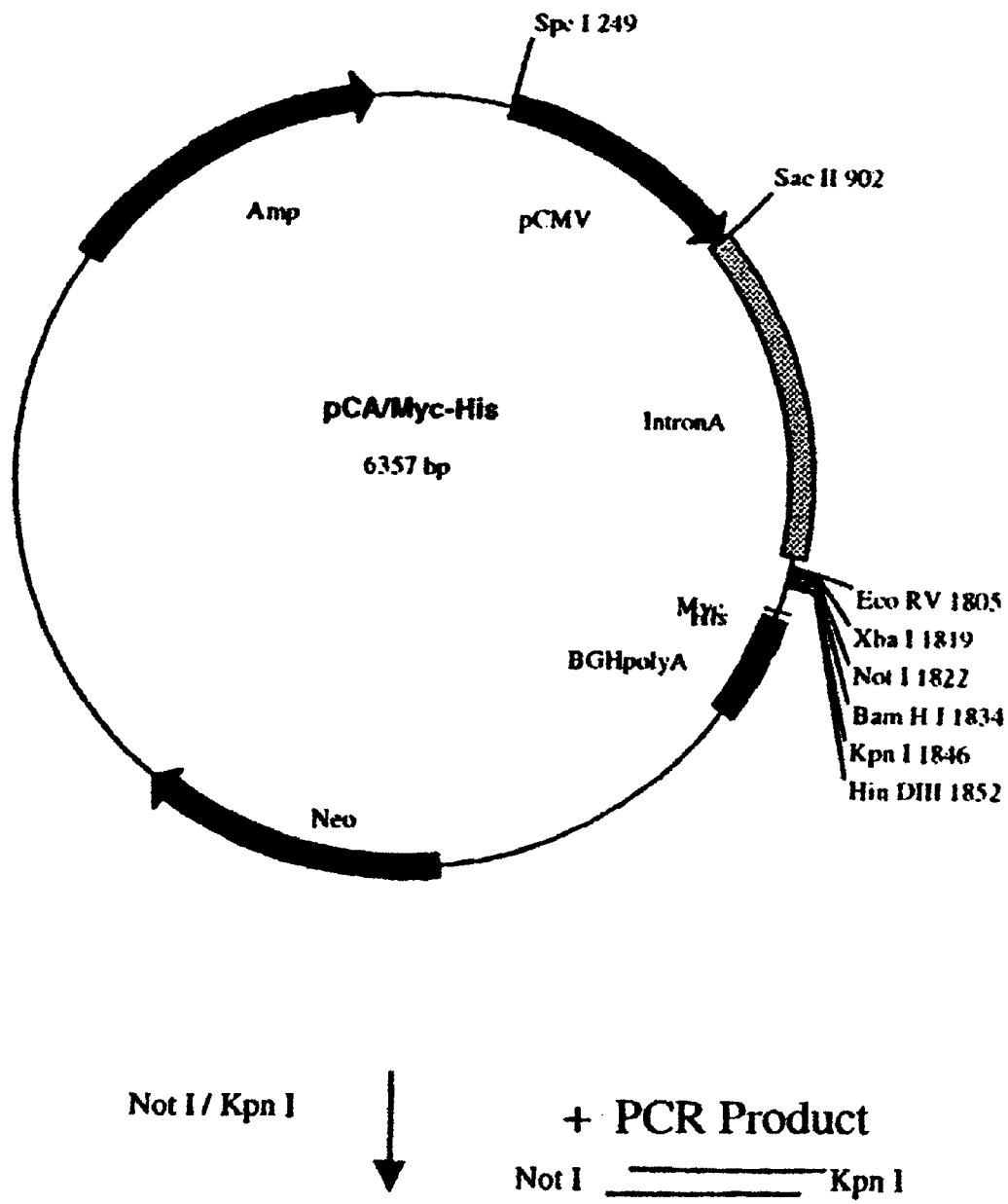
Figure 3C:
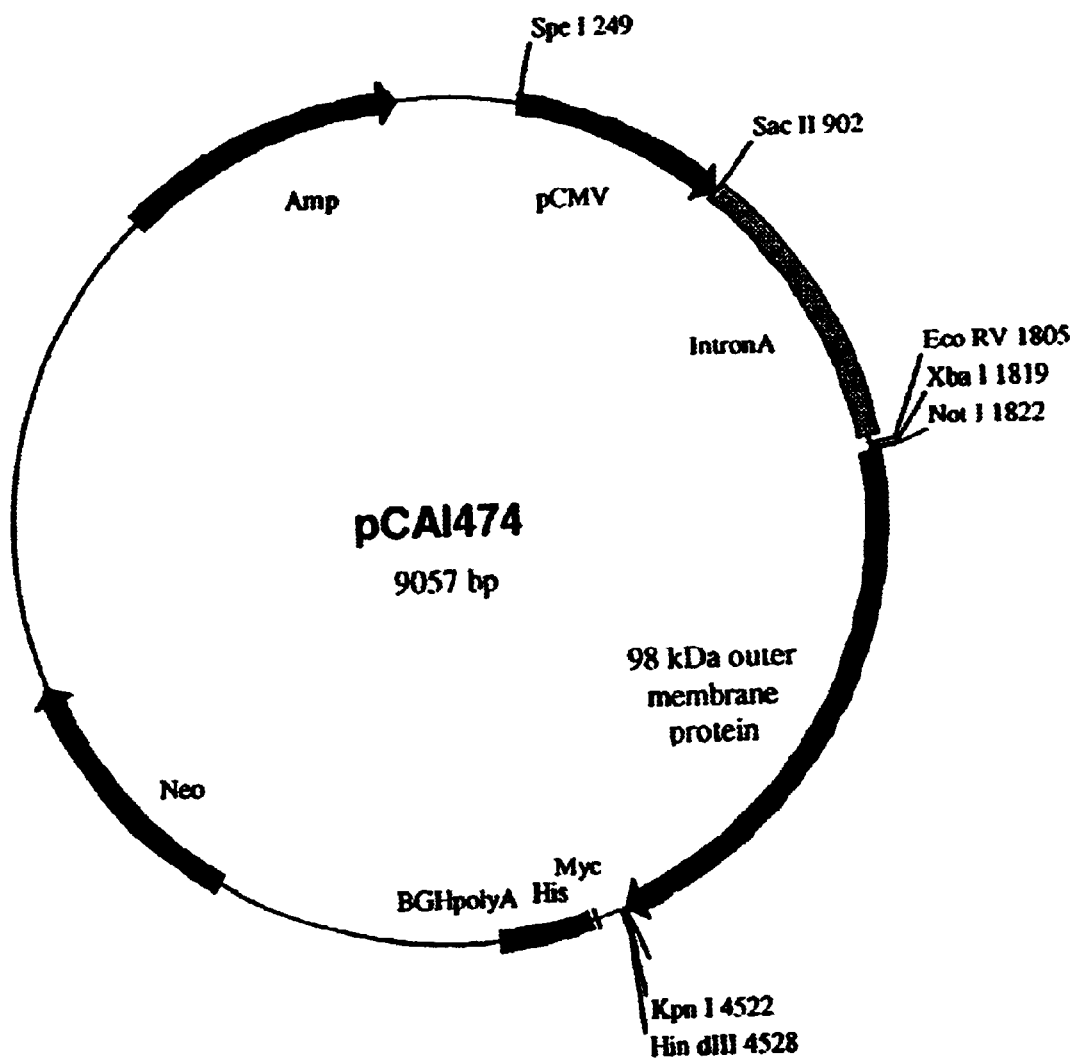
Figure 4:
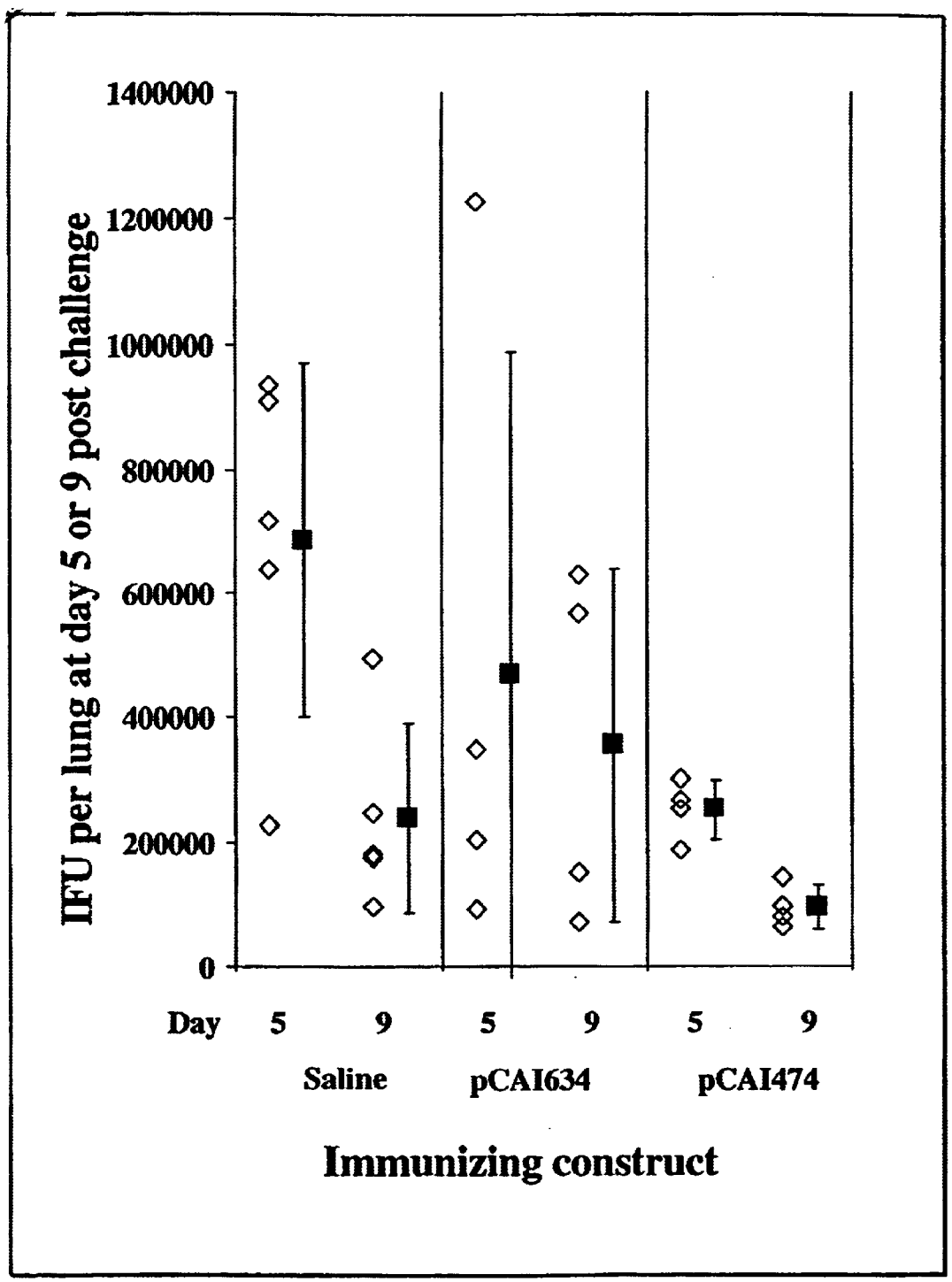

Casey, et al., Nucleic Acids Research, 4:5, 1539–1553 (1977).
Kunkel, Proc. Natl. Acad. Sci. USA, 82, 488–492 (1985).
Langeveld, et al., Vaccine, 12:15, 1994.
Snijders, et al., The Journal of General Virology, 72:3, 557–565 (1991).
Dion, et al., Virology, 179:1, 474–477 (1990).
Hughes, et al., Infection and Immunity, 60:9, 3497–3503 (1992).
Wiedmann–Al–Ahmad, et al., Clinical and Diagnostic Laboratory Immunology, 4:6, 700–704 (1997).
McCafferty, et al., Infection and Immunity, 63:6, 2387–2389 (1995).
Campbell, et al., Infection and Immunity, 58:1, 93–97 (1990).
Cotter, et al., Infection and Immunity, 63:12, 4704–4714 (1995).
Shor, et al, S AFR Med Journal, 82, 158–161 (1992).

* cited by examiner

```
cagatgcttc atctacaaat aaagacgaga agagccttaa tgcttgtagt catggagatc   60
attatcctcc taaaactgta gaagaggaag tgccaccttc atg tta gaa gaa cat  115
                                             Met Leu Glu Glu His
                                              1               5 cct gtt gtt tct tcg aca gat att cgt ggt ggt ggg gcc att cta gct  163
Pro Val Val Ser Ser Thr Asp Ile Arg Gly Gly Gly Ala Ile Leu Ala
            10              15                      20 caa cat atc ttt att aca gat aat aca gga aat ctg aga ttc tct ggg  211
Gln His Ile Phe Ile Thr Asp Asn Thr Gly Asn Leu Arg Phe Ser Gly
                25              30                  35 aac ctt ggt ggt ggt gaa gag tct tct act gtc ggt gat tta gct atc  259
Asn Leu Gly Gly Gly Glu Glu Ser Ser Thr Val Gly Asp Leu Ala Ile
        40                  45                  50 gta gga gga ggt gct ttg ctt tct act aat gaa gtt aat gtt tgc agt  307
Val Gly Gly Gly Ala Leu Leu Ser Thr Asn Glu Val Asn Val Cys Ser
    55                  60                  65 aac caa aat gtt gtt ttt tct gat aac gtg act tca aat ggt tgt gat  355
Asn Gln Asn Val Val Phe Ser Asp Asn Val Thr Ser Asn Gly Cys Asp
 70              75                  80                      85 tca ggg gga gct att tta gct aaa aaa gta gat atc tcc gcg aac cac  403
Ser Gly Gly Ala Ile Leu Ala Lys Lys Val Asp Ile Ser Ala Asn His
                90              95                  100 tcg gtt gaa ttt gtc tct aat ggt tca ggg aaa ttc ggt ggt gcc gtt  451
Ser Val Glu Phe Val Ser Asn Gly Ser Gly Lys Phe Gly Gly Ala Val
            105             110                     115 tgc gct tta aac gaa tca gta aac att acg gac aat ggc tcg gca gta  499
Cys Ala Leu Asn Glu Ser Val Asn Ile Thr Asp Asn Gly Ser Ala Val
            120             125                     130 tca ttc tct aaa aat aga aca cgt ctt ggc ggt gct gga gtt gca gct  547
Ser Phe Ser Lys Asn Arg Thr Arg Leu Gly Gly Ala Gly Val Ala Ala
    135             140                     145
```

FIG. 1A

```
cct caa ggc tct gta acg att tgt gga aat cag gga aac ata gca ttt    595
Pro Gln Gly Ser Val Thr Ile Cys Gly Asn Gln Gly Asn Ile Ala Phe
150             155                 160                 165 aaa gag aac ttt gtt ttt ggc tct gaa aat caa aga tca ggt gga gga    643
Lys Glu Asn Phe Val Phe Gly Ser Glu Asn Gln Arg Ser Gly Gly Gly
            170                 175                 180 gct atc att gct aac tct tct gta aat att cag gat aac gca gga gat    691
Ala Ile Ile Ala Asn Ser Ser Val Asn Ile Gln Asp Asn Ala Gly Asp
                185                 190                 195 atc cta ttt gta agt aac tct acg gga tct tat gga ggt gct att ttt    739
Ile Leu Phe Val Ser Asn Ser Thr Gly Ser Tyr Gly Gly Ala Ile Phe
            200                 205                 210 gta gga tct ttg gtt gct tct gaa ggc agc aac cca cga acg ctt aca    787
Val Gly Ser Leu Val Ala Ser Glu Gly Ser Asn Pro Arg Thr Leu Thr
    215                 220                 225 att aca ggc aac agt ggg gat atc cta ttt gct aaa aat agc acg caa    835
Ile Thr Gly Asn Ser Gly Asp Ile Leu Phe Ala Lys Asn Ser Thr Gln
230                 235                 240                 245 aca gcc gct tct tta tca gaa aaa gat tcc ttt ggt gga ggg gcc atc    883
Thr Ala Ala Ser Leu Ser Glu Lys Asp Ser Phe Gly Gly Gly Ala Ile
                250                 255                 260 tat aca caa aac ctc aaa att gta aag aat gca ggg aac gtt tct ttc    931
Tyr Thr Gln Asn Leu Lys Ile Val Lys Asn Ala Gly Asn Val Ser Phe
            265                 270                 275 tat ggc aac aga gct cct agt ggt gct ggt gtc caa att gca gac gga    979
Tyr Gly Asn Arg Ala Pro Ser Gly Ala Gly Val Gln Ile Ala Asp Gly
            280                 285                 290 gga act gtt tgt tta gag gct ttt gga gga gat atc tta ttt gaa ggg    1027
Gly Thr Val Cys Leu Glu Ala Phe Gly Gly Asp Ile Leu Phe Glu Gly
    295                 300                 305
```

FIG. 1B

| | | | | | | | | | | | | | | |
|---|---|---|---|---|---|---|---|---|---|---|---|---|---|---|
| aat | atc | aat | ttt | gat | ggg | agt | ttc | aat | gcg | att | cac | tta | tgc | ggg | aat | 1075 |
| Asn | Ile | Asn | Phe | Asp | Gly | Ser | Phe | Asn | Ala | Ile | His | Leu | Cys | Gly | Asn |
| 310 | | | | 315 | | | | | 320 | | | | | 325 |

```
aat atc aat ttt gat ggg agt ttc aat gcg att cac tta tgc ggg aat        1075
Asn Ile Asn Phe Asp Gly Ser Phe Asn Ala Ile His Leu Cys Gly Asn
310             315                 320                 325 gac tca aaa atc gta gag ctt tct gct gtt caa gat aaa aat att att        1123
Asp Ser Lys Ile Val Glu Leu Ser Ala Val Gln Asp Lys Asn Ile Ile
                330                 335                 340 ttc caa gat gca att act tat gaa gag aac aca att cgt ggc ttg cca        1171
Phe Gln Asp Ala Ile Thr Tyr Glu Glu Asn Thr Ile Arg Gly Leu Pro
                345                 350                 355 gat aaa gat gtc agt cct tta agt gcc cct tca tta att ttt aac tcc        1219
Asp Lys Asp Val Ser Pro Leu Ser Ala Pro Ser Leu Ile Phe Asn Ser
        360                 365                 370 aag cca caa gat gac agc gct caa cat cat gaa ggg acg ata cgg ttt        1267
Lys Pro Gln Asp Asp Ser Ala Gln His His Glu Gly Thr Ile Arg Phe
        375                 380                 385 tct cga ggg gta tct aaa att cct cag att gct gct ata caa gag gga        1315
Ser Arg Gly Val Ser Lys Ile Pro Gln Ile Ala Ala Ile Gln Glu Gly
390             395                 400                 405 acc tta gct tta tca caa aac gca gag ctt tgg ttg gca gga ctt aaa        1363
Thr Leu Ala Leu Ser Gln Asn Ala Glu Leu Trp Leu Ala Gly Leu Lys
                410                 415                 420 cag gaa aca gga agt tct atc gta ttg tct gcg gga tct att ctc cgt        1411
Gln Glu Thr Gly Ser Ser Ile Val Leu Ser Ala Gly Ser Ile Leu Arg
            425                 430                 435 att ttt gat tcc cag gtt gat agc agt gcg cct ctt cct aca gaa aat        1459
Ile Phe Asp Ser Gln Val Asp Ser Ser Ala Pro Leu Pro Thr Glu Asn
            440                 445                 450 aaa gag gag act ctt gtt tct gcc gga gtt caa att aac atg agc tct        1507
Lys Glu Glu Thr Leu Val Ser Ala Gly Val Gln Ile Asn Met Ser Ser
455                 460                 465
```

FIG. 1C

| | | | | | | | | | | | | | | |
|---|---|---|---|---|---|---|---|---|---|---|---|---|---|---|
| cct | aca | ccc | aat | aaa | gat | aaa | gct | gta | gat | act | cca | gta | ctt | gca | gat | 1555
| Pro | Thr | Pro | Asn | Lys | Asp | Lys | Ala | Val | Asp | Thr | Pro | Val | Leu | Ala | Asp |
| 470 | | | | 475 | | | | | 480 | | | | | | 485 | atc ata agt att act gta gat ttg tct tca ttt gtt cct gag caa gac   1603
Ile Ile Ser Ile Thr Val Asp Leu Ser Ser Phe Val Pro Glu Gln Asp
            490             495                 500 gga act ctt cct ctt cct cct gaa att atc att cct aag gga aca aaa   1651
Gly Thr Leu Pro Leu Pro Pro Glu Ile Ile Ile Pro Lys Gly Thr Lys
                505             510             515 tta cat tct aat gcc ata gat ctt aag att ata gat cct acc aat gtg   1699
Leu His Ser Asn Ala Ile Asp Leu Lys Ile Ile Asp Pro Thr Asn Val
        520             525             530 gga tat gaa aat cat gct ctt cta agt tct cat aaa gat att cca tta   1747
Gly Tyr Glu Asn His Ala Leu Leu Ser Ser His Lys Asp Ile Pro Leu
    535             540             545 att tct ctt aag aca gcg gaa gga atg aca ggg acg cct aca gca gat   1795
Ile Ser Leu Lys Thr Ala Glu Gly Met Thr Gly Thr Pro Thr Ala Asp
550             555             560             565 gct tct cta tct aat ata aaa ata gat gta tct tta cct tcg atc aca   1843
Ala Ser Leu Ser Asn Ile Lys Ile Asp Val Ser Leu Pro Ser Ile Thr
                570             575             580 cca gca acg tat ggt cac aca gga gtt tgg tct gaa agt aaa atg gaa   1891
Pro Ala Thr Tyr Gly His Thr Gly Val Trp Ser Glu Ser Lys Met Glu
            585             590             595 gat gga aga ctt gta gtc ggt tgg caa cct acg gga tat aag tta aat   1939
Asp Gly Arg Leu Val Val Gly Trp Gln Pro Thr Gly Tyr Lys Leu Asn
        600             605             610 cct gag aag caa ggg gct cta gtt ttg aat aat ctc tgg agt cat tat   1987
Pro Glu Lys Gln Gly Ala Leu Val Leu Asn Asn Leu Trp Ser His Tyr
    615             620             625

FIG. 1D

```
aca gat ctt aga gct ctt aag cag gag atc ttt gct cat cat acg ata    2035
Thr Asp Leu Arg Ala Leu Lys Gln Glu Ile Phe Ala His His Thr Ile
630             635             640             645 gct caa aga atg gag tta gat ttc tcg aca aat gtc tgg gga tca gga    2083
Ala Gln Arg Met Glu Leu Asp Phe Ser Thr Asn Val Trp Gly Ser Gly
            650             655             660 tta ggt gtt gtt gaa gat tgt cag aac atc gga gag ttt gat ggg ttc    2131
Leu Gly Val Val Glu Asp Cys Gln Asn Ile Gly Glu Phe Asp Gly Phe
        665             670             675 aaa cat cat ctc aca ggg tat gcc cta ggc ttg gat aca caa cta gtt    2179
Lys His His Leu Thr Gly Tyr Ala Leu Gly Leu Asp Thr Gln Leu Val
        680             685             690 gaa gac ttc tta att gga gga tgt ttc tca cag ttc ttt ggt aaa act    2227
Glu Asp Phe Leu Ile Gly Gly Cys Phe Ser Gln Phe Phe Gly Lys Thr
    695             700             705 gaa agc caa tcc tac aaa gct aag aac gat gtg aag agt tat atg gga    2275
Glu Ser Gln Ser Tyr Lys Ala Lys Asn Asp Val Lys Ser Tyr Met Gly
710             715             720             725 gct gct tat gcg ggg att tta gca ggt cct tgg tta ata aaa gga gct    2323
Ala Ala Tyr Ala Gly Ile Leu Ala Gly Pro Trp Leu Ile Lys Gly Ala
            730             735             740 ttt gtt tac ggt aat ata aac aac gat ttg act aca gat tac ggt act    2371
Phe Val Tyr Gly Asn Ile Asn Asn Asp Leu Thr Thr Asp Tyr Gly Thr
        745             750             755 tta ggt att tca aca ggt tca tgg ata gga aaa ggg ttt atc gca ggc    2419
Leu Gly Ile Ser Thr Gly Ser Trp Ile Gly Lys Gly Phe Ile Ala Gly
        760             765             770 aca agc att gat tac cgc tat att gta aat cct cga cgg ttt ata tcg    2467
Thr Ser Ile Asp Tyr Arg Tyr Ile Val Asn Pro Arg Arg Phe Ile Ser
775             780             785
```

FIG. 1E

```
gca atc gta tcc aca gtg gtt cct ttt gta gaa gcc gag tat gtc cgt    2515
Ala Ile Val Ser Thr Val Val Pro Phe Val Glu Ala Glu Tyr Val Arg
790             795             800             805 ata gat ctt cca gaa att agc gaa cag ggt aaa gag gtt aga acg ttc    2563
Ile Asp Leu Pro Glu Ile Ser Glu Gln Gly Lys Glu Val Arg Thr Phe
            810             815                 820 caa aaa act cgt ttt gag aat gtc gcc att cct ttt gga ttt gct tta    2611
Gln Lys Thr Arg Phe Glu Asn Val Ala Ile Pro Phe Gly Phe Ala Leu
            825             830             835 gaa cat gct tat tcg cgt ggc tca cgt gct gaa gtg aac agt gta cag    2659
Glu His Ala Tyr Ser Arg Gly Ser Arg Ala Glu Val Asn Ser Val Gln
            840             845             850 ctt gct tac gtc ttt gat gta tat cgt aag gga cct gtc tct ttg att    2707
Leu Ala Tyr Val Phe Asp Val Tyr Arg Lys Gly Pro Val Ser Leu Ile
            855             860             865 aca ctc aag gat gct gct tat tct tgg aag agt tat ggg gta gat att    2755
Thr Leu Lys Asp Ala Ala Tyr Ser Trp Lys Ser Tyr Gly Val Asp Ile
870             875             880             885 cct tgt aaa gct tgg aag gct cgc ttg agc aat aat acg gaa tgg aat    2803
Pro Cys Lys Ala Trp Lys Ala Arg Leu Ser Asn Asn Thr Glu Trp Asn
            890             895             900 tca tat tta agt acg tat tta gcg ttt aat tat gaa tgg aga gaa gat    2851
Ser Tyr Leu Ser Thr Tyr Leu Ala Phe Asn Tyr Glu Trp Arg Glu Asp
            905             910             915 ctg ata gct tat gac ttc aat ggt ggt atc cgt att att ttc            2893
Leu Ile Ala Tyr Asp Phe Asn Gly Gly Ile Arg Ile Ile Phe
            920             925             930 tagttcgatg tgacagggct tcaatcaaaa aaaagggtta cttttagtaa ccctttttta  2953
tttctcttaa tgcttatagt tcgatgatct ttaatacata gagcaagtag gcgatacaag  3013
ctttattagg ttcataggtc tctgggtcca ttaagag                           3050
```

FIG. 1F

```
                            MnlI
                          Pfl1108I
                           HphI    |
                           MnlI    |
                           AluI    |   |
         TaaI              CviJI   |   |         BseRI Tth111II   MseI
          |                 | ||   |   |           |     |         |
              TGTCGGTGATTTAGCTATCGTAGGAGGAGGTGCTTTGCTTTCTACTAATGAAGTTAATGT
         241 ----------+----------+----------+----------+----------+----------+ 300
              ACAGCCACTAAATCGATAGCATCCTCCTCCACGAAACGAAAGATGATTACTTCAATTACA

MaeIII
                                         Tsp45I
                               Bsp24I      |
                                CjeI       |
         MaeIII                 CjePI      |            HinfI
         CviRI  |             Hpy188IX|MaeII|            TfiI  Bsp24I
           | |                    ||   ||                 |      |
              TTGCAGTAACCAAAATGTTGTTTTTTCTGATAACGTGACTTCAAATGGTTGTGATTCAGG
         301 ----------+----------+----------+----------+----------+----------+ 360
              AACGTCATTGGTTTTACAACAAAAAGACTATTGCACTGAAGTTTACCAACACTAAGTCC . AluI
              CviJI      AluI                 DrdII
              CjeI    |  CviJI  |             ThaI   |        ApoI
          CjePI|  |   |  MwoI   |       EcoRV AciI   |        Tsp509I
              ||| |   |   ||    |         |    ||    |          |
              GGGAGCTATTTTAGCTAAAAAGTAGATATCTCCGCGAACCACTCGGTTGAATTTGTCTC
         361 ----------+----------+----------+----------+----------+----------+ 420
              CCCTCGATAAAATCGATTTTTTCATCTATAGAGGCGCTTGGTGAGCCAACTTAAACAGAG DraI
                                                       MseI|
             DrdII       ApoI                          CjePI||
             CjePI   |   Tsp509I   NlaIV       HhaI    |||HinfI
           BsmAI |   |   Bcef I    BanI   |   MwoI     | || TfiI CjeI
                ||   |     ||       |         |        | |||  |   |
              TAATGGTTCAGGGAAATTCGGTGGTGCCGTTTGCGCTTTAAACGAATCAGTAAACATTAC
         421 ----------+----------+----------+----------+----------+----------+ 480
              ATTACCAAGTCCCTTTAAGCCACCACGGCAAACGCGAAATTTGCTTAGTCATTTGTAATG
```

FIG. 2B

```
                                                            MwoI
                                                      BseRI  |
       CviJI                              MaeII       Bce83I | |
    Hin4I |              CjeI CjeI        AflIII  AciI  |    | |
      | |                 |    |           |  |    |    |    | |
      GGACAATGGCTCGGCAGTATCATTCTCTAAAAATAGAACACGTCTTGGCGGTGCTGGAGT
481   ---------+---------+---------+---------+---------+---------+ 540
      CCTGTTACCGAGCCGTCATAGTAAGAGATTTTTATCTTGTGCAGAACCGCCACGACCTCA

MaeIII
                MnlI|
      AluI    AceIII ||
      CviJI    BpmI  ||
    Fnu4HI |   CviJI ||
     CjeI|     BbvI| ||
     CviRI|    CjeI|| ||                              DraI
     TseI| |SmlI ||| ||                    CjeI       MseI|
      || |  |   ||| ||                      |          ||
      TGCAGCTCCTCAAGGCTCTGTAACGATTTGTGGAAATCAGGGAAACATAGCATTTAAAGA
541   ---------+---------+---------+---------+---------+---------+ 600
      ACGTCGAGGAGTTCCGAGACATTGCTAAACACCTTTAGTCCCTTTGTATCGTAAATTTCT

BseRI
                                                      MboII |
                                                      MwoI| |
                                                      BsrDI|| |
                           MnlI            AluI        ||| |
              Hpy188IX     DpnI|           CviJI       ||| |
              CviJI  |    Sau3AI||         Hin4I|      ||| |
                |    |      |  ||           ||  |      ||| |
      GAACTTTGTTTTTGGCTCTGAAAATCAAAGATCAGGTGGAGGAGCTATCATTGCTAACTC
601   ---------+---------+---------+---------+---------+---------+ 660
      CTTGAAACAAAAACCGAGACTTTTAGTTTCTAGTCCACCTCCTCGATAGTAACGATTGAG

MnlI
                                                         DpnI|
                                                         BstYI ||
              Hpy178III                    Sth132I       Sau3AI ||
      EarI SspI    |            EcoRV      MaeIII|       BscGI| ||
       |    |      |              |           ||          || ||
      TTCTGTAAATATTCAGGATAACGCAGGAGATATCCTATTTGTAAGTAACTCTACGGGATC
661   ---------+---------+---------+---------+---------+---------+ 720
      AAGACATTTATAAGTCCTATTGCGTCCTCTATAGGATAAACATTCATTGAGATGCCCTAG
```

FIG. 2C

```
                              DpnI
              BstYI  |        Hpy188IX  Fnu4HI              Eco57I
     AlwI     Sau3AI |  AlwI  |         TseI|               BbvI    |
      |        |  |     |     |         | |                  |      |
            TTATGGAGGTGCTATTTTTGTAGGATCTTTGGTTGCTTCTGAAGGCAGCAACCCACGAAC
721   ---------+---------+---------+---------+---------+---------+  780
            AATACCTCCACGATAAAAACATCCTAGAAACCAACGAAGACTTCCGTCGTTGGGTGCTTG

AciI
                            EcoRV                                Fnu4HI
                   TspRI   |                                     TauI
     Tsp509I   TaaI    |   |                       Cac8I         CviJI|
        |      |       |   |                         |              ||
            GCTTACAATTACAGGCAACAGTGGGGATATCCTATTTGCTAAAAATAGCACGCAAACAGC
781   ---------+---------+---------+---------+---------+---------+  840
            CGAATGTTAATGTCCGTTGTCACCCCTATAGGATAAACGATTTTTATCGTGCGTTTGTCG

BccI
                                          CviJI  |
                                          HaeIII |
                                          Hin4I| |
              Hpy188IX     HinfI          NlaIV| |
     Tth111I I         |   TfiI   MnlI    Sau96I|||                Tsp509I
        | |            |   |      |           |||                     |
            CGCTTCTTTATCAGAAAAAGATTCCTTTGGTGGAGGGGCCATCTATACACAAAACCTCAA
841   ---------+---------+---------+---------+---------+---------+  900
            GCGAAGAAATAGTCTTTTTCTAAGGAAACCACCTCCCCGGTAGATATGTGTTTTGGAGTT BfaI
                                                      BanII   |
                                                      BsiHKAI |
                                                      Bsp1286I|
                                                      SacI    |
                     BsmI  AclI                       AluI    | |
     MnlI   CviRI    |MaeII                           CviJI   | | |
      |      | |     |                                  |     | | |
            AATTGTAAAGAATGCAGGGAACGTTTCTTTCTATGGCAACAGAGCTCCTAGTGGTGCTGG
901   ---------+---------+---------+---------+---------+---------+  960
            TTAACATTTCTTACGTCCCTTGCAAAGAAAGATACCGTTGTCTCGAGGATCACCACGACC
```

FIG. 2D

```
                Tth111II
       CviRI       MnlI
                   |       TaaI    |      CviJI        EcoRV
  Tsp509I MnlI     |  BsaXI |      |       MnlI      Hin4I        |  BseRI
    |    |         |    |   |      |        |          |         |    |
      TGTCCAAATTGCAGACGGAGGAACTGTTTGTTTAGAGGCTTTTGGAGGAGATATCTTATT
  961 ----------+----------+----------+----------+----------+----------+ 1020
      ACAGGTTTAACGTCTGCCTCCTTGACAAACAAATCTCCGAAAACCTCCTCTATAGAATAA

FauI
                                            Sth132I|
                                             HinfI ||            PleI
          Tsp509I          BccI               TfiI ||   AciI  |  HinfI
             |              |                  |   ||    |    |    |
      TGAAGGGAATATCAATTTTGATGGGAGTTTCAATGCGATTCACTTATGCGGGAATGACTC
 1021 ----------+----------+----------+----------+----------+----------+ 1080
      ACTTCCCTTATAGTTAAAACTACCCTCAAAGTTACGCTAAGTGAATACGCCCTTACTGAG AluI
            CviJI                          SfaNI            Tsp509I
      Pfl1108I  |      Hpy178III    SspI   |                CviRI|    EarI
         |      |          |          |    |                  |  |     |
      AAAAATCGTAGAGCTTTCTGCTGTTCAAGATAAAAATATTATTTTCCAAGATGCAATTAC
 1081 ----------+----------+----------+----------+----------+----------+ 1140
      TTTTTAGCATCTCGAAAGACGACAAGTTCTATTTTTATAATAAAAGGTTCTACGTTAATG Bsp1286I
                  MboII    Cac8I                             BmgI  |
        CjeI    Tsp509I |  CviJI  |          CjeI          MseI BseSI |
          |        |    |    |    |            |             |    |   |
      TTATGAAGAGAACACAATTCGTGGCTTGCCAGATAAAGATGTCAGTCCTTTAAGTGCCCC
 1141 ----------+----------+----------+----------+----------+----------+ 1200
      AATACTTCTCTTGTGTTAAGCACCGAACGGTCTATTTCTACAGTCAGGAAATTCACGGGG Tsp509I                                 HaeII    NlaIII
        MseI|                                 HhaI|Hpy178III  |
       VspI|      MseI        CviJI          Eco47III||  RcaI |  |
         ||       |             |                |||     |    |  |
      TTCATTAATTTTTAACTCCAAGCCACAAGATGACAGCGCTCAACATCATGAAGGGACGAT
 1201 ----------+----------+----------+----------+----------+----------+ 1260
      AAGTAATTAAAAATTGAGGTTCGGTGTTCTACTGTCGCGAGTTGTAGTACTTCCCTGCTA
```

FIG. 2E

```
             BanII
             BsiHKAI
             Bsp1286I             SfcI
                SacI              AluI|
               AluI |              CviJI|                RsaI
              CviJI |             TaqII||                ScaI
             NlaIII |              BaeI|||       TatI    |          EcoRV
                | | |       BpmI     ||||       BsrI |  |CviRI     |    BaeI
                | | |         |      ||||        |   |   |         |     |
             GAGCTCTCCTACACCCAATAAAGATAAAGCTGTAGATACTCCAGTACTTGCAGATATCAT
       1501  ---------+---------+---------+---------+---------+---------+ 1560
             CTCGAGAGGATGTGGGTTATTTCTATTTCGACATCTATGAGGTCATGAACGTCTATAGTA

BbsI                    Bpu10I
                    MboII                    DdeI
                     TaaI |           Hpy178III         PpiI
                     SfcI| |           BseMII       MboII MboII |EarI   EarI
                       ||| |             |            |    |    |  |     |
             AAGTATTACTGTAGATTTGTCTTCATTTGTTCCTGAGCAAGACGGAACTCTTCCTCTTCC
       1561  ---------+---------+---------+---------+---------+---------+ 1620
             TTCATAATGACATCTAAACAGAAGTAAACAAGGACTCGTTCTGCCTTGAGAAGGAGAAGG

MseI
                                                                 AflII|
                                                                  SmlI|
                    MnlI                                          DpnI ||
             Tsp509I  |                                           BglII | ||
            Hpy178III |      Bsu36I                              BstYI | ||
               MnlI   |        DdeI    Tsp509I    MsII           Sau3AI | ||  AlwI
                | |   |         |        |         |               |    | ||   |
             TCCTGAAATTATCATTCCTAAGGGAACAAAATTACATTCTAATGCCATAGATCTTAAGAT
       1621  ---------+---------+---------+---------+---------+---------+ 1680
             AGGACTTTAATAGTAAGGATTCCCTTGTTTTAATGTAAGATTACGGTATCTAGAATTCTA

DpnI
             RleAI
             BstYI |
             Sau3AI |                                    EarI
             HaeIV | |                         NlaIII    SapI
             Hin4I | |                 MboII    |        DdeI|
               | | |                    |       |          ||
             TATAGATCCTACCAATGTGGGATATGAAAATCATGCTCTTCTAAGTTCTCATAAAGATAT
       1681  ---------+---------+---------+---------+---------+---------+ 1740
             ATATCTAGGATGGTTACACCCTATACTTTTAGTACGAGAAGATTCAAGAGTATTTCTATA
```

FIG. 2G

```
         Tsp509I        MseI                                 SfcI
           MseI|       AflII|     AciI                      SfaNI  |  BsmFI
           VspI|        SmlI|    MspA1I              BsaHI  |  |HgaI   |
            ||           ||      |                   |  |  |  |        |
          TCCATTAATTTCTCTTAAGACAGCGGAAGGAATGACAGGGACGCCTACAGCAGATGCTTC
     1741 ---------+---------+---------+---------+---------+---------+ 1800
          AGGTAATTAAAGAGAATTCTGTCGCCTTCCTTACTGTCCCTGCGGATGTCGTCTACGAAG

DpnI              MaeIII
                                 Sau3AI |                  Tsp45I
                                   TaqI| |         MaeII          |
                                    || |              |           |
          TCTATCTAATATAAAAATAGATGTATCTTTACCTTCGATCACACCAGCAACGTATGGTCA
     1801 ---------+---------+---------+---------+---------+---------+ 1860
          AGATAGATTATATTTTTATCTACATAGAAATGGAAGCTAGTGTGGTCGTTGCATACCAGT

Sth132I
                                                        MboII     |
                                                   AhdI   |       |
                                                   BbsI|  |       |
                                                   HaeIV|  |      |
                                                   Hin4I|  |      |
                Hpy188IX               BccI  MboII  ||    |       |
                   |                     |     | ||       |       |
          CACAGGAGTTTGGTCTGAAAGTAAAATGGAAGATGGAAGACTTGTAGTCGGTTGGCAACC
     1861 ---------+---------+---------+---------+---------+---------+ 1920
          GTGTCCTCAAACCAGACTTTCATTTTACCTTCTACCTTCTGAACATCAGCCAACCGTTGG

DdeI        BfaI
                        Hpy178III      BanII|
                  MseI       |       Bsp1286I|                Hinf I
          BscGI  BseMII|     |        CviJI ||             Hpy178III  |
            |     ||    |    |          |  ||                 |  |
                TACGGGATATAAGTTAAATCCTGAGAAGCAAGGGGCTCTAGTTTTGAATAATCTCTGGAG
     1921 ---------+---------+---------+---------+---------+---------+ 1980
          ATGCCCTATATTCAATTTAGGACTCTTCGTTCCCCGAGATCAAAACTTATTAGAGACCTC
```

FIG. 2H

```
                                    MboII
                         Tsp509I |
                            MnlI |  |
               BfaI         MseI |  |           FokI
    BslI       SpeI|        BbsI ||  |           TaaI
     |          ||            | || |              |
         CTTGGATACACAACTAGTTGAAGACTTCTTAATTGGAGGATGTTTCTCACAGTTCTTTGG
2161     ---------+---------+---------+---------+---------+---------+ 2220
         GAACCTATGTGTTGATCAACTTCTGAAGAATTAACCTCCTACAAAGAGTGTCAAGAAACC

PauI
                                                              Fnu4HI|
                                                             Sth132I|
                                                                AluI||
                            DdeI                                CviJI||
                            AluI|             BbvI              TseI||
               CviJI        CviJI|    EarI  AceIII|     MboII      |||
                 |            ||        |     ||          |        |||
         TAAAACTGAAAGCCAATCCTACAAAGCTAAGAACGATGTGAAGAGTTATATGGGAGCTGC
2221     ---------+---------+---------+---------+---------+---------+ 2280
         ATTTTGACTTTCGGTTAGGATGTTTCGATTCTTGCTACACTTCTCAATATACCCTCGACG

BsaJI
                         StyI
                        AvaII   |
                       EcoO109I |
              BspMI     Psp5II  |              BsaXI
              AciI  |   Sau96I  |               AluI  |
      MwoI    |     |  Sse8647I |    MseI      CviJI  |     TaaI
       |      |     |     |     |     |          |   |      |
         TTATGCGGGGATTTTAGCAGGTCCTTGGTTAATAAAAGGAGCTTTTGTTTACGGTAATAT
2281     ---------+---------+---------+---------+---------+---------+ 2340
         AATACGCCCCTAAAATCGTCCAGGAACCAATTATTTTCCTCGAAAACAAATGCCATTATA

RsaI
                SfcI         TaaI |                    NlaIII
                 |            |   |                      |
         AAACAACGATTTGACTACAGATTACGGTACTTTAGGTATTTCAACAGGTTCATGGATAGG
2341     ---------+---------+---------+---------+---------+---------+ 2400
         TTTGTTGCTAAACTGATGTCTAATGCCATGAAATCCATAAAGTTGTCCAAGTACCTATCC

Tth111I                      MnlI
                Cac8I                 AciI  |          TaqI  TaaI  |
                  |                     |   |           |     |    |
         AAAAGGGTTTATCGCAGGCACAAGCATTGATTACCGCTATATTGTAAATCCTCGACGGTT
2401     ---------+---------+---------+---------+---------+---------+ 2460
         TTTTCCCAAATAGCGTCCGTGTTCGTAACTAATGGCGATATAACATTTAGGAGCTGCCAA
```

FIG. 2J

```
                                    NlaIV                                    DpnI
                                    TspRI                                    BglII  |
                                    DrdII|                                   BstYI  |
                                    BciVI||               CjePI              Sau3AI |
                CjePI         TaaI  |||                   CviJI    MboII     |      ||
                  |            |    |||                   |  |       |       |      ||
               TATATCGGCAATCGTATCCACAGTGGTTCCTTTTGTAGAAGCCGAGTATGTCCGTATAGA
       2461    ---------+---------+---------+---------+---------+---------+    2520
               ATATAGCCGTTAGCATAGGTGTCACCAAGGAAAACATCTTCGGCTCATACAGGCATATCT

Tsp509I                              AclI
              Hpy178III  |             MnlI            MaeII
                 |  |                   |                |
              TCTTCCAGAAATTAGCGAACAGGGTAAAGAGGTTAGAACGTTCCAAAAAACTCGTTTTGA
       2521   ---------+---------+---------+---------+---------+---------+   2580
              AGAAGGTCTTTAATCGCTTGTCCCATTTCTCCAATCTTGCAAGGTTTTTTGAGCAAAACT

BsaAI
                                                                       PmlI
                                                                       MaeII|
                                           NlaIII              CviJI   |    ||
                                           NspI        ThaI    |       |    ||
                                            |           |      |       |    ||
              GAATGTCGCCATTCCTTTTGGATTTGCTTTAGAACATGCTTATTCGCGTGGCTCACGTGC
       2581   ---------+---------+---------+---------+---------+---------+   2640
              CTTACAGCGGTAAGGAAAACCTAAACGAAATCTTGTACGAATAAGCGCACCGAGTGCACG

Cac8I
                         Eco57I
                         AluI  |
                         CviJI |
                   TspRI  |    |                                        Bce83I
                   RsaI|  |    |                               NlaIV    |
                   BsrGI|| |   |                               AvaII|
                   TatI || |   |                               EcoO109I|
                   TaaI |'|  | |         MaeII     BsaBI       Psp5II|
                     |   |||  | |          |          |        Sau96I|  |
                     |   |||  | |          |          |          |   ||  |
              TGAAGTGAACAGTGTACAGCTTGCTTACGTCTTTGATGTATATCGTAAGGGACCTGTCTC
       2641   ---------+---------+---------+---------+---------+---------+   2700
              ACTTCACTTGTCACATGTCGAACGAATGCAGAAACTACATATAGCATTCCCTGGACAGAG
```

FIG. 2K

```
              BbvI
           SfaNI              CjePI
     BsmFI   |         Fnu4HI |EarI
     BsmAI | |SmlI     TseI|  |FokI         MboII        CjePI
     | |   | |         | |  | |             |            |
         TTTGATTACACTCAAGGATGCTGCTTATTCTTGGAAGAGTTATGGGGTAGATATTCCTTG
2701    ----------+----------+----------+----------+----------+----------+  2760
         AAACTAATGTGAGTTCCTACGACGAATAAGAACCTTCTCAATACCCCATCTATAAGGAAC

SmlI            ApoI           BsaAI
       AluI    Cac8I   |               Bce83I         SnaBI
       CviJI   CviJI | |               EcoRI          MaeII|
  HindIII |    MwoI | | |              Tsp509I   MseI RsaI||
     | |  |    |  | | | |              |         |    | |||
         TAAAGCTTGGAAGGCTCGCTTGAGCAATAATACGGAATGGAATTCATATTTAAGTACGTA
2761    ----------+----------+----------+----------+----------+----------+  2820
         ATTTCGAACCTTCCGAGCGAACTCGTTATTATGCCTTACCTTAAGTATAAATTCATGCAT Hpy188IX
                                   DpnI  |
                              BglII  |   |
                              BstYI  |   |  AluI
             Tsp509I          Sau3AI |   |  CviJI
             MseI|            Hin4I  |   |  MboII
             | |              |  |   |   |  |
         TTTAGCGTTTAATTATGAATGGAGAGAAGATCTGATAGCTTATGACTTCAATGGTGGTAT
2821    ----------+----------+----------+----------+----------+----------+  2880
         AAATCGCAAATTAATACTTACCTCTCTTCTAGACTATCGAATACTGAAGTTACCACCATA MaeIII
                    Tsp45I
       BciVI BfaI TaqI  |         CviJI           MaeIII         MaeIII
       |     |    |     |         |               |              |
         CCGTATTATTTTCTAGTTCGATGTGACAGGGCTTCAATCAAAAAAAAGGGTTACTTTTAG
2881    ----------+----------+----------+----------+----------+----------+  2940
         GGCATAATAAAAGATCAAGCTACACTGTCCCGAAGTTAGTTTTTTTTCCCAATGAAAATC
```

FIG. 2L

```
                                              DpnI
                                           Sau3AI |
                        MseI             TaqI  | |MseI
                         |                 |   | | |
         TAACCCTTTTTTATTTCTCTTAATGCTTATAGTTCGATGATCTTTAATACATAGAGCAAG
2941     ---------+---------+---------+---------+---------+---------+ 3000
         ATTGGGAAAAAATAAAGAGAATTACGAATATCAAGCTACTAGAAATTATGTATCTCGTTC

NlaIV
                                             AvaII|
                     AluI                   Sau96I|
                     CviJI                   SimI|
                  HindIII |                  BsaI ||
                    MwoI| |                 BsmAI ||| MseI
                      || |                    | ||| |
         TAGGCGATACAAGCTTTATTAGGTTCATAGGTCTCTGGGTCCATTAAGAG
3001     ---------+---------+---------+---------+---------+ 3050
         ATCCGCTATGTTCGAAATAATCCAAGTATCCAGAGACCCAGGTAATTCTC
```

FIG. 2M

CHLAMYDIA ANTIGENS AND CORRESPONDING DNA FRAGMENTS AND USES THEREOF

RELATED U.S. APPLICATION

The present patent application claims priority to the following U.S. provisional patent applications: U.S. Ser. Nos. 60/106,046, filed Oct. 28, 1998 and Ser. No. 60/132, 271, filed May 3, 1999, each incorporated herein by reference.

FIELD OF THE INVENTION

The present invention relates to Chlamydia antigens and corresponding DNA molecules, which can be used in methods to prevent and treat disease caused by Chlamydia infection in mammals, such as humans.

BACKGROUND OF THE INVENTION

Chlamydiae are prokaryotes. They exhibit morphologic and structural similarities to Gram negative bacteria including a trilaminar outer membrane, which contains lipopolysaccharide and several membrane proteins. Chlamydiae are differentiated from other bacteria by their morphology and by a unique developmental cycle. They are obligate intracellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells they were long thought to be viruses. However, they have many characteristics in common with other bacteria: (1) they contain both DNA and RNA, (2) they divide by binary fission, (3) their cell envelopes resemble those of other Gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man, and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomatis* has a high degree of host specificity, being almost completely limited to man; it causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *C. psittaci*, but subsequently recognized to be a new species. *C. pneumoniae* is antigenically, genetically, and morphologically distinct from other Chlamydia species (*C. trachomatis, C. pecorum* and *C. psittaci*). It shows 10% or less DNA sequence homology with either of *C. trachomatis* or *C. psittaci* and so far appears to consist of only a single strain, TWAR.

*C. pneumoniae* is a common cause of community acquired pneumonia, less frequent only than *Streptococcus pneumoniae* and *Mycoplasma pneumoniae*. Grayston et al., *J. Infect. Dis.* 168: 1231 (1995); Campos et al., *Invest. Ophthalmol. Vis. Sci.* 36: 1477 (1995), each incorporated herein by reference. It can also cause upper respiratory tract symptoms and disease, including bronchitis and sinusitis. See, e.g., Grayston et al., *J. Infect. Dis.* 168: 1231 (1995); Campos et al., *Invest. Ophthalmol. Vis. Sci.* 36: 1477 (1995); Grayston et al., *J. Infect. Dis.* 161: 618 (1990); Marrie, *Clin. Infect. Dis.* 18: 501 (1993). The great majority of the adult population (over 60%) has antibodies to *C. pneumoniae* (Wang et al., *Chlamydial Infections*, Cambridge University Press, Cambridge, p. 329 (1986)), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/day, for at least 10 to 14 days). A recently developed drug, azithromycin, is highly effective as a single-dose therapy against chlamydial infections.

In most instances, *C. pneumoniae* infection is mild and without complications, and up to 90% of infections are subacute or unrecognized. Among children in industrialized countries, infections have been thought to be rare up to the age of five years, although a recent study has reported that many children in this age group show PCR evidence of infection despite being seronegative, and estimates a prevalence of 17–19% in 2–4 years old. See, Normann et al., *Acta Paediatrica*, 87: 23–27 (1998). In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 years. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease. See, Saikku et al., *Lancet* 2: 983 (1988); Thom et al., *JAMA* 268: 68 (1992); Linnanmaki et al., *Circulation* 87: 1030 (1993); Saikku et al., *Annals Int. Med.* 116: 273 (1992); Melnick et al., *Am. J. Med.* 95: 499 (1993). Moreover, the organisms has been detected in atheromas and fatty streaks of the coronary, carotid, peripheral arteries and aorta. See, Shor et al., *South African Med. J.* 82: 158 (1992); Kuo et al., *J. Infect. Dis.* 167: 841 (1993); Kuo et al., *Arteriosclerosis and Thrombosis* 13: 1500 (1993); Campbell et al., *J. Infect. Dis.* 172: 585 (1995); Chiu et al., *Circulation* 96: 2144–2148 (1997). Viable *C. pneumoniae* has been recovered from the coronary and carotid artery. Ramirez et al., *Annals Int. Med.* 125: 979 (1996); Jackson et al., Abst. K121, p272, 36th ICAAC, New Orleans (1996). Furthermore, it has been shown that *C. pneumoniae* can induce changes of atherosclerosis in a rabbit model. See, Fong et al., (1997) *Journal of Clinical Microbiolology* 35: 48. Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbation of asthma in adults, and small-scale studies have shown that prolonged antibiotic treatment was effective at greatly reducing the severity of the disease in some individuals. Hahn et al., *Ann Allergy Asthma Immunol.* 80: 45–49 (1998); Hahn et al., *Epidemiol Infect.* 117: 513–517 (1996); Bjornsson et al., *Scand J. Infect. Dis.* 28: 63–69 (1996); Hahn, *J. Fam. Pract.* 41: 345–351 (1995); Allegra et al., *Eur. Respir. J.* 7: 2165–2168 (1994); Hahn et al., *JAMA* 266: 225–230 (1991).

In light of these results, a protective vaccine against disease caused by *C. pneumoniae* infection would be of considerable importance. There is not yet an effective vaccine for human *C. pneumoniae* infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge. Pal et al., *Infection and Immunity* 64: 5341 (1996). Similarly, sheep immunized with inactivated *C. psittaci* were protected from subsequent chlamydial-induced abortions and stillbirths. Jones et al., *Vaccine* 13: 715 (1995). Protection from chlamydial infections has been associated with Th1 immune responses, particularly the induction of INFγ-producing CD4+ T cells. Igietsemes et al., *Immunology* 5: 317 (1993). The adoptive transfer of CD4+ cell lines or clones to nude or SCID mice conferred protection from challenge or cleared chronic disease (Igietseme et al., *Regional Immunology* 5: 317 (1993); Magee et al., *Regional Immunology* 5: 305 (1993)), and in vivo depletion of CD4+ T cells exacerbated disease post-challenge (Landers et al., *Infection & Immunity* 59: 3774 (1991); Magee et al., *Infection & Immunity* 63: 516 (1995)). However, the presence of sufficiently high titres of neutralizing antibody at mucosal surfaces can also exert a protective effect. Cotter et al., *Infection and Immunity* 63: 4704 (1995).

The extent of antigenic variation within the species *C. pneumoniae* is not well characterized. Serovars of *C. trachomatis* are defined on the basis of antigenic variation in major outer membrane proteins (MOMP), but published *C. pneumoniae* MOMP gene sequences show no variation between several diverse isolates of the organism. See, Campbell et al., *Infection and Immunity* 58: 93 (1990); McCafferty et al., *Infection and Immunity* 63: 2387–9 (1995); Knudsen et al., Third Meeting of the European Society for Chlamydia Research, Vienna (1996). Regions of the protein known to be conserved in other chlamydial MOMPs are conserved in *C. pneumoniae*. See, Campbell et al., *Infection and Immunity* 58: 93 (1990); McCafferty et al., *Infection and Immunity* 63: 2387–9 (1995). One study has described a strain of *C. pneumoniae* with a MOMP of greater that usual molecular weight, but the gene for this has not been sequenced. Grayston et al., *J. Infect. Dis.* 168: 1231 (1995). Partial sequences of outer membrane protein 2 from nine diverse isolates were also found to be invariant. Ramirez et al., *Annals Int. Med.* 125: 979 (1996). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes. Marrie, *Clin. Infect. Dis.* 18: 501 (1993).

Many antigens recognized by immune sera to *C. pneumoniae* are conserved across all chlamydiae, but 98 kDa, 76 kDa and 54 kda proteins may be *C. pneumoniae*-specific. Campos et al., *Invest. Ophthalmol. Vis. Sci.* 36: 1477 (1995); Marrie, *Clin. Infect. Dis.* 18: 501 (1993); Wiedmann-Al-Ahmad et al., *Clin. Diagn. Lab. Immunol.* 4: 700–704 (1997). Immunoblotting of isolates with sera from patients does show variation of blotting patterns between isolates, indicating that serotypes *C. pneumoniae* may exist. Grayston et al., *J. Infect. Dis.* 168: 1231 (1995); Ramirez et al., *Annals Int. Med.* 125: 979 (1996). However, the results are potentially confounded by the infection status of the patients, since immunoblot profiles of a patient's sera change with time post-infection. An assessment of the number and relative frequency of any serotypes, and the defining antigens, is not yet possible.

Thus, a need remains for effective compositions for preventing, treating, and diagnosing Chlamydia infections.

SUMMARY OF THE INVENTION

In one aspect, the present invention provides purified and isolated DNA molecules that encode Chlamydia which can be used in methods to prevent, treat, and diagnose Chlamydia infection. Encoded polypeptides, designated 98 kDa outer membrane protein, include polypeptides having the amino acid sequence shown in SEQ ID NO: 2 and the DNA molecules include SEQ ID NO: 1 full-length sequence (top sequence) and coding sequence (bottom sequence) for the mature polypeptide. Those skilled in the art will appreciate that the invention also includes DNA molecules that encode mutants, variants, and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vectors such as viral or bacterial live vaccine vectors, including, pox virus, alphavirus, *Salmonella typhimurium*, or *Vibrio cholerae* vector, containing a polynucleotide of the invention, such vaccine vectors being useful for, e.g., preventing and treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography.The present invention provides purified and isolated DNA molecules, which encode Chlamydia that can be used in methods to prevent, treat, and diagnose Chlamydia infection.

BRIEF DESCRIPTION OF THE DRAWINGS

The present invention will be further understood from the following description with reference to the drawings, in which:

FIGS. 1A–1F show the nucleotide sequence (top sequence) and the deduced amino acid sequence (bottom sequence) of the full length 98 kDa outer membrane protein gene (SEQ ID NO: 1) and the processed sequence from *Chlamydia pneumoniae* (SEQ ID NO: 2).

FIGS. 2A–2M show the restriction enzyme analysis of nucleotide sequence encoding the *C. pneumoniae* 98 kDa outer membrane protein gene.

FIG. 3 shows the construction and elements of plasmid pCAI474.

FIG. 4 illustrates protection against *C. pneumoniae* infection by pCAI474 following DNA immunization. Individual data points are shown for each animal (hollow diamonds) as well as mean and standard deviation for each group (solid squares).

DETAILED DESCRIPTION OF THE INVENTION

In the *C. pneumoniae* genome, open reading frames (ORFs) encoding chlamydial polypeptides have been identified. These polypeptides include polypeptides permanently found in the bacterial membrane structure, polypeptides that are present in the external vicinity of the bacterial membrane, include polypeptides permanently found in the inclusion membrane structure, polypeptides that are present in the external vicinity of the inclusion membrane, and polypeptides that are released into the cytoplasm of the infected cell. These polypeptides can be used in vaccination methods for preventing and treating Chlamydia infection.

According to a first aspect of the invention, there are provided isolated polynucleotides encoding the precursor and mature forms of Chlamydia polypeptides.

An isolated polynucleotide of the invention encodes a polypeptide having an amino acid sequence that is homologous to a Chlamydia amino acid sequence, the Chlamydia amino acid sequence being selected from the group consisting of the amino acid sequences as shown in SEQ ID NOS: 1 and 2.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides could be part of a vector or a composition and still be isolated in that such a vector or composition is not part of its natural environment.

A polynucleotide of the invention can be in the form of RNA or DNA (e.g., cDNA, genomic DNA, or synthetic DNA), or modifications or combinations thereof. The DNA can be double-stranded or single-stranded, and, if single-stranded, can be the coding strand or the non-coding (anti-sense) strand. The sequence that encodes a polypeptide of the invention as shown in SEQ ID NO: 1 can be (a) the coding sequence (bottom sequence); (b) a ribonucleotide sequence derived by transcription of (a); or (c) a different coding sequence. This latter, as a result of the redundancy or degeneracy of the genetic code, encodes the same polypeptides as the DNA molecules of which the nucleotide sequences are illustrated in SEQ ID NOS: 1 or 2.

By "homologous amino acid sequence" is meant an amino acid sequence that differs from an amino acid sequence shown in SEQ ID NO: 2, only by one or more conservative amino acid substitutions, or by one or more non-conservative amino acid substitutions, deletions, or additions located at positions at which they do not destroy the specific antigenicity of the polypeptide.

Preferably, such a sequence is at least 75%, more preferably 80%, and most preferably 90% identical to an amino acid sequence shown in SEQ ID NO: 2.

Homologous amino acid sequences include sequences that are identical or substantially identical to an amino acid sequence as shown in SEQ ID NO: 2. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM250 matrix described in Dayhoff et al., 5 *Atlas of Protein Sequence and Structure* 345–352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Preferably, a homologous sequence is one that is at least 45%, more preferably 60%, and most preferably 85% identical to the coding sequence of SEQ ID NO: 1.

Polypeptides having a sequence homologous to one of the sequences shown in SEQ ID NOS: 1 and 2, include naturally-occurring allelic variants, as well as mutants and variants or any other non-naturally-occurring variants that are analogous in terms of antigenicity, to a polypeptide having a sequence as shown in SEQ ID NOS: 1 or 2.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NOS: 1 and 2, to the extent that the fragments retain the desired substantial antigenicity of the parent polypeptide (specific antigenicity). Polypeptide derivatives can also be constructed by large internal deletions that remove a substantial part of the parent polypeptide, while retaining the desired specific antigenicity. Generally, polypeptide derivatives should be about at least 12 amino acids in length to maintain the antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. Hughes et al., *Infect. Immun.* 60: 3497 (1992).

Polypeptide fragments and polypeptides having large internal deletions can be used for revealing epitopes that are otherwise masked in the parent polypeptide and that may be of importance for inducing, for example, a protective T cell-dependent immune response. Deletions can also remove immunodominant regions of high variability among strains.

It is an accepted practice in the field of immunology to use fragments and variants of protein immunogens as vaccines and immunogens, as all that is required to induce an immune response to a protein may be a small (e.g., 8 to 10 amino acid) region of the protein. This has been done for a number of vaccines against pathogens other than Chlamydia. For example, short synthetic peptides corresponding to surface-exposed antigens of pathogens such as murine mammary tumor virus, peptide containing 11 amino acids (Dion et al., *Virology* 179: 474–477 (1990)); Semliki Forest virus, peptide containing 16 amino acids (Snijders et al., *J. Gen. Virol.* 72: 557–565 (1991)); and canine parvovirus, two overlapping peptides, each containing 15 amino acids (Langeveld et al., *Vaccine* 12: 1473–1480 (1994)) have been shown to be effective vaccine antigens against their respective pathogens.

Polynucleotides encoding polypeptide fragments and polypeptides having large internal deletions can be constructed using standard methods (see, e.g., Ausubel et al., *Current Protocols in Molecular Biology*, John Wiley & Sons Inc. (1994)); for example, by PCR, including inverse PCR, by restriction enzyme treatment of the cloned DNA molecules, or by the method of Kunkel et al. (*Proc. Natl. Acad. Sci. USA* 82: 448 (1985)); biological material available at Stratagene.

A polypeptide derivative can also be produced as a fusion polypeptide that contains a polypeptide or a polypeptide derivative of the invention fused, e.g., at the N- or C-terminal end, to any other polypeptide. For construction of DNA encoding the amino acid sequence corresponding to hybrid fusion proteins, a first DNA encoding amino acid sequence corresponding to portions of SEQ ID NO: 1 or 2 is joined to a second DNA using methods described in, for example, U.S. Pat. No. 5,844,095, incorporated herein by reference. A product can then be easily obtained by translation of the genetic fusion. Vectors for expressing fusion polypeptides are commercially available, such as the pMal-c2 or pMal-p2 systems of New England Biolabs, in which the fusion peptide is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in the invention includes a polypeptide or polypeptide derivative of the invention fused to a polypeptide having adjuvant activity, such as, e.g., the subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NO: 1. Hybridization procedures are described in, e.g., Ausubel et al., *Current Procotols in Molecular Biology*, John Wiley & Sons Inc. (1994); Silhavy et al., *Experiments with Gene Fusions*, Cold Spring Harbor Laboratory Press (1984); Davis et al., *A Manual for Genetic Engineering: Advance Bacterial Genetics*, Cold Spring Harbor Laboratory Press (1980), each incorporated herein by reference. Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows:

$$Tm = 81.5 + 0.5 \times (\% \ G+C) + 1.6 \log (\text{positive ion concentration}) - 0.6 \times (\% \ \text{formamide}).$$

Under appropriate stringency conditions, hybridization temperature (Th) is approximately 20–40° C., 20–25° C. or, preferably, 30–40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)).

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows:

$$Tm = 4 \times (G+C) + 2 \ (A+T).$$

For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can overexpress a polynucleotide of the invention or express it in a modified, mutated form, such as a non-toxic form, if appropriate. For vaccine compositions and uses of the proteins and peptides and encoding nucleotides of the present invention for protection against diseases caused by Chlamydia, it is not preferred to use naked DNA encoding the protein or peptides and administering these nucleotides intranasally or intramuscularly. For these proteins, it is preferred to administer the encoding nucleic acids by other routes such as intradermally and/or to formulate the encoding nucleic acids to improve (or adjuvant) the immune response. It is also preferred to include the encoding nucleic acid as part of a recombinant live vector, such as a viral or bacterial vector for use as the immunizing agent. It is also preferred to immunize with vaccine formulations comprising the proteins or peptides of the invention themselves. These vaccine formulations may include the use of adjuvants.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a prokaryotic or eukaryotic cell transformed or transfected with an expression cassette and/or vector of the invention, as well as (iv) a process for producing a polypeptide or polypeptide derivative encoded by a polynucleotide of the invention, which involves culturing a prokaryotic or eukaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from prokaryotic and eukaryotic hosts. Eukaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a prokaryotic host such as *E. coli* is used. Bacterial and eukaryotic cells are available from a number of different sources to those skilled in the art, e.g., the American Type Culture Collection (ATCC; Rockville, Md.).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., *Protein Engineering* 4: 843 (1991)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and R1pB lipidation signal peptide (Takase et al., *J. Bact.* 169: 5692 (1987)).

The expression cassette is typically part of an expression vector, which is selected for its ability to replicate in the chosen expression system. Expression vectors (e.g., plasmids or viral vectors) can be chosen from those described in Pouwels et al. (*Cloning Vectors: Laboratory Manual*, 85, Supp. 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumonia, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses, alphavirus, and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., Tartaglia et al., *Virology* 188: 217 (1992)) for a description of a vaccinia virus vector; and Taylor et al, *Vaccine* 13: 539 (1995) for a reference of a canary pox). Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in three doses, four weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306: 551 (1983) and U.S. Pat. No. 4,882,278 (strain in which a substantial amount of the coding sequence of each of the two ctxA alleles has been deleted so that no functional *cholerae* toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1 \times 10^5$ to about $1 \times 10^9$, preferably about $1 \times 10^6$ to about $1 \times 10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., *Bio/Technology* 6: 693 (1988) and WO 92/11361. Preferred routes of administration include all mucosal routes; most preferably, these vectors are administered intranasally or orally.

Others bacterial strains useful as vaccine vectors are described in High et al., *EMBO* 11: 1991 (1992); Sizemore et al., *Science* 270: 299 (1995) (*Shigella flexneri*); Medaglini et al., *Proc. Natl. Acad. Sci. USA* 92: 6868 (1995) (*Streptococcus gordonii*); and Flynn, *Cell. Mol. Biol.* 40: 31 (1994), WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis*, *C. psittaci*, *C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168, 062) and the Rous Sarcoma Virus promoter (described in Norton & Coffin, *Molec. Cell Biol.* 5: 281(1985)). The desmin promoter (Li et al., *Gene* 78: 243 (1989), Li & Paulin, *J. Biol. Chem.* 266: 6562 (1991), and Li & Paulin, *J. Biol. Chem.* 268: 10403 (1993)) is tissue-specific and drives expression in muscle cells. More generally, useful vectors are described, i.a., WO 94/21797 and Hartikka et al., *Human Gene Therapy* 7:1205 (1996).

For DNA/RNA vaccination, the polynucleotide of the invention can encode a precursor or a mature form. When it encodes a precursor form, the precursor form can be homologous or heterologous. In the latter case, a eukaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., *Liposomes: A Practical Approach*, RPC New Ed, IRL Press (1990)), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in, e.g., WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (*Nature* 356: 152 (1992)). In this case, the microparticle-coated polynucleotides can be injected via intradermal or intra-epidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 μg to about 1 mg, preferably, from about 10 μg to about 800 μg and, more preferably, from about 25 μg to about 250 μg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NO: 1.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., *Science* 254: 1497 (1991)) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., *Molecular Cloning: A Laboratory Manual* (1982) Cold Spring Harbor Laboratory Press, Cold Spring Harbor, N.Y.), Southern blot (Southern, *J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NOS: 1 and 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli, *Nature* 227: 680 (1970). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCl (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia;

and particularly, (iv) a method for preventing and/or treating a Chlamydia (e.g., C. trachomatis. C. psittaci, C. pneumoniae. or C. pecorum) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the subcutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see *Liposomes: A Practical Approach* (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., *Current Protocols in Immunology* (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., *Antibodies: A Laboratory Manual*, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided: (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3 b-(N-(N',N'-dimethyl aminomethane)-carbamoyl) cholesterol (U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen + adjuvant can be administered on days 7, 14,21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation. Polypeptides having a sequence homologous to one of the sequences shown in SEQ ID NOS: 1 and 2, include naturally-occurring allelic variants, as well as mutants or any other non-naturally occurring variants that are analogous in terms of antigenicity, to a polypeptide.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NO: 1, to the extent that the fragments retain the substantial antigenicity of the parent polypeptide (specific antigenicity). Polypeptide derivatives can also be constructed by large internal deletions that remove a substantial part of the parent polypeptide, while retaining specific antigenicity. Generally, polypeptide derivatives should be about at least 12 amino acids in length to maintain antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. See e.g.,Hughes et al., *Infect. Immun.* 60(9):3497 1992.

Polypeptide fragments and polypeptides having large internal deletions can be used for revealing epitopes that are otherwise masked in the parent polypeptide and that may be of importance for inducing a protective T cell-dependent immune response. Deletions can also remove immunodominant regions of high variability among strains.

It is an accepted practice in the field of immunology to use fragments and variants of protein immunogens as vaccines, as all that is required to induce an immune response to a protein is a small (e.g., 8 to 10 amino acid) immunogenic region of the protein. This has been done for a number of vaccines against pathogens other than Chlamydia. For example, short synthetic peptides corresponding to surface-exposed antigens of pathogens such as murine mammary tumor virus, peptide containing 11 amino acids; (see e.g., Dion et al., *Virology* 179:474–477 (1990)) Semliki Forest virus, peptide containing 16 amino acids (see e.g., Snijders et al., *J. Gen. Virol.* 72:557–565 (1991)), and canine parvovirus, 2 overlapping peptides, each containing 15 amino acids (see e.g., Langeveld et al. *Vaccine* 12(15):1473–1480 (1994)), have been shown to be effective vaccine antigens against their respective pathogens.

Polynucleotides encoding polypeptide fragments and polypeptides having large internal deletions can be constructed using standard methods, for example, by PCR, including inverse PCR, by restriction enzyme treatment of the cloned DNA molecules, or by the method of Kunkel et al. (*Proc. Natl. Acad. Sci. USA* 82:448 (1985)) using biological material available at Stratagene.

A polypeptide derivative can also be produced as a fusion polypeptide that contains a polypeptide or a polypeptide derivative of the invention fused, e.g., at the N- or C-terminal end, to any other polypeptide (hereinafter referred to as a peptide tail). Such a product can be easily obtained by translation of a genetic fusion, i.e., a hybrid gene. Vectors for expressing fusion polypeptides are commercially available, such as the pMal-c2 or pMal-p2 systems of New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in invention includes a polypeptide or polypeptide derivative of the invention fused to a polypeptide having adjuvant activity, such as, e.g., subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NOS: 1 or 2. Hybridization procedures are, e.g., described in Ausubel et al., *Current Protocols in Molecular Biology*, John Wiley & Sons Inc. (1994), Silhavy et al. *Experiments with Gene Fusions*, Cold Spring Harbor Laboratory Press (1984); Davis et al., *A Manual for Genetic Engineering: Advanced Bacterial Genetics*, Cold Spring Harbor Laboratory Press (1980). Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows: $Tm=81.5+0.41\times(\% \, G+C)+16.6 \log(\text{cation ion concentration})-0.63\times(\% \, \text{formamide})-600/\text{base number}$. Under appropriate stringency conditions, hybridization temperature (Th) is approximately 20–40° C., 20–25° C., or, preferably 30–40° C. below the calculated Tm. Those skilled in the a understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g.,65° C. At such a temperature, stringent hybridization conditions can be achieved in 6×SSC, preferably in 2×SSC or 1×SSC, more preferably in 0.5×SSC, 0.3×SSC or 0.1×SSC (in the absence of formamide). 1×SSC contains 0.15 M NaCl and 0.015 M sodium citrate.

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows: $Tm=4\times(G+C)+2(A+T)$. For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can over-express a polynucleotide of the invention or express it in a non-toxic, mutated form.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a procaryotic host such as *E. coli* is used. Bacterial and eucaryotic cells are available from a number of different sources to those skilled in the art, e.g., the American Type Culture Collection (ATCC; Rockville, Md.).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., *Protein Engineering* 4: 843 (1991); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide. See Takase et al., *J. Bact.* 169: 5692 (1987).

The expression cassette is typically part of an expression vector, which is selected for its ability to replicate in the chosen expression system. Expression vectors (e.g., plasmids or viral vectors) can be chosen from those described in Pouwels et al. (Cloning Vectors: A Laboratory Manual 1985, Supp. 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994)).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumoniae, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively. Also see, e.g., Tartaglia et al., *Virology* 188: 217 (1992) for a description of a vaccinia virus vector; and Taylor et al, *Vaccine* 13: 539 (1995) for a reference of a canary pox. Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306:551 (1983) and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1\times10^5$ to about $1\times10^9$, preferably about $1\times10^6$ to about $1\times10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., Bio/Technology 6:693 (1998) and WO 92/11361. Preferred routes of administration include all mucosal routes; most preferably, these vectors are administered intranasally or orally.

Others bacterial strains useful as vaccine vectors are described in High et al., EMBO (1992) 11:1991 and Sizemore et al., Science (1995) 270:299 (*Shigella flexneri*); Medaglini et al., *Proc. Natl. Acad. Sci. USA* (1995) 92:6868 (*Streptococcus gordonii*); and Flynn, *Cell. Mol. Biol.* (1994) 40 (suppl. I):31, WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol.* 5:281 (1985)). The desmin promoter (Li et al., *Gene* 78: 243 (1989); Li & Paulin,*J. Biol. Chem.* 266: 6562 (1991); and Li & Paulin,*J. Biol. Chem.* 268: 10403 (1993)) is tissue-specific and drives expression in muscle cells. More generally, useful vectors are described, i.a., WO 94/21797 and Hartikka et al., *Human Gene Therapy* 7: 1205 (1996).

For DNA/RNA vaccination, the polynucleotide of the invention can encode a precursor or a mature form. When it encodes a precursor form, the precursor form can be homologous or heterologous. In the latter case, a eucaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen such as urease subunit A, B, or both; or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., Liposomes: A Practical Approach, RPC New Ed, IRL Press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as, for example, described in WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (Nature (1992) 356:152). In this case, the microparticle-coated polynucleotides can be injected via intradermal or intraepidermal routes using a needleless injection device ("gene gun"), such as those described in U.S. Pat. No. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NOS: 1 or 2.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., Science (1991) 254:1497) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, *J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NO: 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli (*Nature* 25 227: 680 (1970)). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis. C. psittaci, C. pneumoniae.* or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the sub-cutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPS) to facilitate delivery and/or enhance the immune response. These compounds are readily available to one skilled in the art; for example, see Liposomes: A Practical Approach (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 μg to about 500 mg, preferably from about 1 mg to about 200 mg. For the parenteral route of administration, the dose usually should not exceed about 1 mg, preferably about 100 μg.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., Antibodies: A Laboratory Manual, D. Lane, E. Harlow, Eds. (1988).

Briefly, a biological sample, such as an C. pneumoniae extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M MgCl$_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3 b-(N-(N',N'-dimethyl aminomethane)-carbamoyl) cholesterol; U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7, 14,21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLE 1

Preparation of Plasmid Vector pCAI474 Containing the 98 kDa Outer Membrane Protein Gene This example illustrates the preparation of a plasmid vector pCAI474 containing the 98 kDa outer membrane protein gene.

The 98 kDa outer membrane protein gene was amplified from *Chlamydia pneumoniae* genomic DNA by polymerase chain reaction (PCR) using a 5' primer:

(5'ATAAGAAT GCGGCCGCCACCATGTTAGAAGAACATCCTG TTG 3')

(SEQ ID NO: 3 ), which contains a Not I restriction site, a ribosome binding site, an initiation codon and a sequence at the 5' end of the 98 kDa outer membrane protein coding sequence, and a 3' primer:

(5'CGGGGTACCGGAAAATAATACGGATACCACC 3')

(SEQ ID NO: 4). The 3' primer includes the sequence encoding the C-terminal sequence of the 98 kDa outer membrane protein gene and a Kpn I restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Kpn I and cloned into the pCA-Myc-His eukaryotic expression vector describe in example 2 (FIG. 3) with transcription under control of the human CMV promoter.

EXAMPLE 2

Preparation of the Eukaryotic Expression Vector pCA/Myc-His

This example illustrates the preparation of the eukaryotic expression vector pCA/Myc-His.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Kpn I restricted PCR fragment containing the 98 kDa outer membrane protein gene was ligated into the Not I and Kpn I restricted plasmid pCA/Myc-His to produce plasmid pCAI474 (FIG. 3).

The resulting plasmid, pCAI474, was transferred by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

EXAMPLE 3

Protection Against Intranasal *C. pneumoniae*

This example illustrates the immunization of mice to achieve protection against an intranasal challenge of *C. pneumoniae.*

It has been previously demonstrated (Yang et. al., 1993) that mice are susceptible to intranasal infection with different isolates of *C. pneumoniae*. Strain AR-39 (Grayston, 1989) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* 98 kDa outer membrane protein gene as described in Example 1 and 2. Saline or the plasmid vector lacking an inserted chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenized in SPG buffer (7.5% sucrose, 5 mM glutamate, 12.5 mM phosphate pH 7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

FIG. 4 and Table 1 show that mice immunized i.n. and i.m. with pCAI474 had chlamydial lung titers less than 300,000 in 4 of 4 cases at day 5, and less than 144,000 in 4 of 4 cases at day 9. In contrast, the range of values for control mice sham immunized with saline was 227,000–935,000 IFU/lung (mean 685,240) at day 5 and 96,000–494,000 IFU/lung (mean 238,080) at day 9. DNA immunisation per se was not responsible for the observed protective effect since another plasmid DNA construct, pCAI634, failed to protect, with lung titers in immunized mice similar to those obtained for saline-immunized control mice. The construct pCAI634 is identical to pCAI474 except that the nucleotide sequence encoding the 98 kDa outer membrance protein gene is replaced with a *C. pneumoniae* nucleotide sequence encoding a different putative 98 kDa outer membrane protein.

TABLE 1

Bacterial Load (Inclusion-Forming Units per Lung) in the Lungs of BALB/C Mice Immunized with Various DNA Immunization Constructs

| | Immunizing Construct | | | | | |
|---|---|---|---|---|---|---|
| Mouse | Saline Day 5 | Saline Day 9 | pCAI634 Day 5 | pCAI634 Day 9 | pCAI474 Day 5 | pCAI474 Day 9 |
| 1 | 934200 | 494000 | 1228400 | 151900 | 252600 | 143400 |
| 2 | 638800 | 180500 | 203300 | 70900 | 187200 | 63100 |
| 3 | 226800 | 245400 | 92900 | 567000 | 266200 | 79400 |
| 4 | 908800 | 174500 | 348600 | 628800 | 299200 | 95800 |
| 5 | 717600 | 96000 | | | | |
| MEAN | 685240 | 238080 | 468300 | 354650 | 251300 | 95425 |
| SD | 285189.07 | 152555.91 | 517439.29 | 283943.87 | 46999.72 | 34657.60 |

EQUIVALENTS

From the foregoing detailed description of the specific embodiments of the invention, it should be apparent that a unique Chlamydia antigen has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An isolated polynucleotide comprising a polynucleotide from a strain of Chlamydia selected from the group consisting of:

(a) a polynucleotide comprising the nucleotide sequence of SEQ ID NO:1; and (b) a polynucleotide which hybridizes under stringent hybridizing conditions of 6×SSC containing 50% formamide at 42° C. with a polynucleotide that has a complementary sequence to SEQ ID NO:1, wherein said isolated polynucleotide, when administered in an immunogenically-effective amount to a mammal, induces a mucosal immune response by said mammal against *Chlamydia pneumoniae.*

2. The polynucleotide of claim 1, linked to a second nucleotide sequence encoding a fusion polypeptide.

3. The polynucleotide of claim 2 wherein the fusion polypeptide is a heterologous signal peptide.

4. The polynucleotide of claim 2 wherein the polynucleotide encodes the polypeptide of SEQ ID NO:2.

5. An expression cassette, comprising the polynucleotide of claim 1 operably linked to a promoter.

6. An expression vector, comprising the expression cassette of claim 5.

7. A host cell, comprising the expression cassette of claim 5.

8. The host cell of claim 7, wherein said host cell is a prokaryotic cell.

9. The host cell of claim 7, wherein said host cell is a eukaryotic cell.

10. A method for producing a recombinant polypeptide, comprising:

(a) culturing a host cell of claim 7, under conditions that allow the expression of the recombinant polypeptide;

(b) expressing the recombinant polypeptide; and (c) recovering the expressed recombinant polypeptide.

* * * * *

SEQUENCE LISTING

```
<160> NUMBER OF SEQ ID NOS: 4

<210> SEQ ID NO 1
<211> LENGTH: 3050
<212> TYPE: DNA
<213> ORGANISM: Chlamydia pneumoniae
<220> FEATURE:
<221> NAME/KEY: CDS
<222> LOCATION: (101)..(2893)

<400> SEQUENCE: 1
cagatgcttc atctacaaat aaagacgaga agagccttaa tgcttgtagt catggagatc       60
attatcctcc taaaactgta gaagaggaag tgccaccttc atg tta gaa gaa cat      115
                                              Met Leu Glu Glu His
                                                1               5 cct gtt gtt tct tcg aca gat att cgt ggt ggt ggg gcc att cta gct      163
Pro Val Val Ser Ser Thr Asp Ile Arg Gly Gly Gly Ala Ile Leu Ala
             10                  15                  20 caa cat atc ttt att aca gat aat aca gga aat ctg aga ttc tct ggg      211
Gln His Ile Phe Ile Thr Asp Asn Thr Gly Asn Leu Arg Phe Ser Gly
     25                  30                  35 aac ctt ggt ggt ggt gaa gag tct tct act gtc ggt gat tta gct atc      259
Asn Leu Gly Gly Gly Glu Glu Ser Ser Thr Val Gly Asp Leu Ala Ile
 40                  45                  50 gta gga gga ggt gct ttg ctt tct act aat gaa gtt aat gtt tgc agt      307
Val Gly Gly Gly Ala Leu Leu Ser Thr Asn Glu Val Asn Val Cys Ser
         55                  60                  65 aac caa aat gtt gtt ttt tct gat aac gtg act tca aat ggt tgt gat      355
Asn Gln Asn Val Val Phe Ser Asp Asn Val Thr Ser Asn Gly Cys Asp
 70                  75                  80                  85 tca ggg gga gct att tta gct aaa aaa gta gat atc tcc gcg aac cac      403
Ser Gly Gly Ala Ile Leu Ala Lys Lys Val Asp Ile Ser Ala Asn His
             90                  95                 100 tcg gtt gaa ttt gtc tct aat ggt tca ggg aaa ttc ggt ggt gcc gtt      451
Ser Val Glu Phe Val Ser Asn Gly Ser Gly Lys Phe Gly Gly Ala Val
            105                 110                 115
```

-continued

```
tgc gct tta aac gaa tca gta aac att acg gac aat ggc tcg gca gta        499
Cys Ala Leu Asn Glu Ser Val Asn Ile Thr Asp Asn Gly Ser Ala Val
        120                 125                 130 tca ttc tct aaa aat aga aca cgt ctt ggc ggt gct gga gtt gca gct        547
Ser Phe Ser Lys Asn Arg Thr Arg Leu Gly Gly Ala Gly Val Ala Ala
135                 140                 145 cct caa ggc tct gta acg att tgt gga aat cag gga aac ata gca ttt        595
Pro Gln Gly Ser Val Thr Ile Cys Gly Asn Gln Gly Asn Ile Ala Phe
150                 155                 160                 165 aaa gag aac ttt gtt ttt ggc tct gaa aat caa aga tca ggt gga gga        643
Lys Glu Asn Phe Val Phe Gly Ser Glu Asn Gln Arg Ser Gly Gly Gly
                170                 175                 180 gct atc att gct aac tct tct gta aat att cag gat aac gca gga gat        691
Ala Ile Ile Ala Asn Ser Ser Val Asn Ile Gln Asp Asn Ala Gly Asp
                    185                 190                 195 atc cta ttt gta agt aac tct acg gga tct tat gga ggt gct att ttt        739
Ile Leu Phe Val Ser Asn Ser Thr Gly Ser Tyr Gly Gly Ala Ile Phe
                200                 205                 210 gta gga tct ttg gtt gct tct gaa ggc agc aac cca cga acg ctt aca        787
Val Gly Ser Leu Val Ala Ser Glu Gly Ser Asn Pro Arg Thr Leu Thr
215                 220                 225 att aca ggc aac agt ggg gat atc cta ttt gct aaa aat agc acg caa        835
Ile Thr Gly Asn Ser Gly Asp Ile Leu Phe Ala Lys Asn Ser Thr Gln
230                 235                 240                 245 aca gcc gct tct tta tca gaa aaa gat tcc ttt ggt gga ggg gcc atc        883
Thr Ala Ala Ser Leu Ser Glu Lys Asp Ser Phe Gly Gly Gly Ala Ile
                250                 255                 260 tat aca caa aac ctc aaa att gta aag aat gca ggg aac gtt tct ttc        931
Tyr Thr Gln Asn Leu Lys Ile Val Lys Asn Ala Gly Asn Val Ser Phe
                265                 270                 275 tat ggc aac aga gct cct agt ggt gct ggt gtc caa att gca gac gga        979
Tyr Gly Asn Arg Ala Pro Ser Gly Ala Gly Val Gln Ile Ala Asp Gly
                280                 285                 290 gga act gtt tgt tta gag gct ttt gga gga gat atc tta ttt gaa ggg       1027
Gly Thr Val Cys Leu Glu Ala Phe Gly Gly Asp Ile Leu Phe Glu Gly
            295                 300                 305 aat atc aat ttt gat ggg agt ttc aat gcg att cac tta tgc ggg aat       1075
Asn Ile Asn Phe Asp Gly Ser Phe Asn Ala Ile His Leu Cys Gly Asn
310                 315                 320                 325 gac tca aaa atc gta gag ctt tct gct gtt caa gat aaa aat att att       1123
Asp Ser Lys Ile Val Glu Leu Ser Ala Val Gln Asp Lys Asn Ile Ile
                330                 335                 340 ttc caa gat gca att act tat gaa gag aac aca att cgt ggc ttg cca       1171
Phe Gln Asp Ala Ile Thr Tyr Glu Glu Asn Thr Ile Arg Gly Leu Pro
                345                 350                 355 gat aaa gat gtc agt cct tta agt gcc cct tca tta att ttt aac tcc       1219
Asp Lys Asp Val Ser Pro Leu Ser Ala Pro Ser Leu Ile Phe Asn Ser
            360                 365                 370 aag cca caa gat gac agc gct caa cat cat gaa ggg acg ata cgg ttt       1267
Lys Pro Gln Asp Asp Ser Ala Gln His His Glu Gly Thr Ile Arg Phe
375                 380                 385 tct cga ggg gta tct aaa att cct cag att gct gct ata caa gag gga       1315
Ser Arg Gly Val Ser Lys Ile Pro Gln Ile Ala Ala Ile Gln Glu Gly
390                 395                 400                 405 acc tta gct tta tca caa aac gca gag ctt tgg ttg gca gga ctt aaa       1363
Thr Leu Ala Leu Ser Gln Asn Ala Glu Leu Trp Leu Ala Gly Leu Lys
                410                 415                 420 cag gaa aca gga agt tct atc gta ttg tct gcg gga tct att ctc cgt       1411
Gln Glu Thr Gly Ser Ser Ile Val Leu Ser Ala Gly Ser Ile Leu Arg
```

```
                      425                 430                 435
att ttt gat tcc cag gtt gat agc agt gcg cct ctt cct aca gaa aat       1459
Ile Phe Asp Ser Gln Val Asp Ser Ser Ala Pro Leu Pro Thr Glu Asn
            440                 445                 450 aaa gag gag act ctt gtt tct gcc gga gtt caa att aac atg agc tct       1507
Lys Glu Glu Thr Leu Val Ser Ala Gly Val Gln Ile Asn Met Ser Ser
455                 460                 465 cct aca ccc aat aaa gat aaa gct gta gat act cca gta ctt gca gat       1555
Pro Thr Pro Asn Lys Asp Lys Ala Val Asp Thr Pro Val Leu Ala Asp
470                 475                 480                 485 atc ata agt att act gta gat ttg tct tca ttt gtt cct gag caa gac       1603
Ile Ile Ser Ile Thr Val Asp Leu Ser Ser Phe Val Pro Glu Gln Asp
            490                 495                 500 gga act ctt cct ctt cct cct gaa att atc att cct aag gga aca aaa       1651
Gly Thr Leu Pro Leu Pro Pro Glu Ile Ile Ile Pro Lys Gly Thr Lys
            505                 510                 515 tta cat tct aat gcc ata gat ctt aag att ata gat cct acc aat gtg       1699
Leu His Ser Asn Ala Ile Asp Leu Lys Ile Ile Asp Pro Thr Asn Val
            520                 525                 530 gga tat gaa aat cat gct ctt cta agt tct cat aaa gat att cca tta       1747
Gly Tyr Glu Asn His Ala Leu Leu Ser Ser His Lys Asp Ile Pro Leu
535                 540                 545 att tct ctt aag aca gcg gaa gga atg aca ggg acg cct aca gca gat       1795
Ile Ser Leu Lys Thr Ala Glu Gly Met Thr Gly Thr Pro Thr Ala Asp
550                 555                 560                 565 gct tct cta tct aat ata aaa ata gat gta tct tta cct tcg atc aca       1843
Ala Ser Leu Ser Asn Ile Lys Ile Asp Val Ser Leu Pro Ser Ile Thr
            570                 575                 580 cca gca acg tat ggt cac aca gga gtt tgg tct gaa agt aaa atg gaa       1891
Pro Ala Thr Tyr Gly His Thr Gly Val Trp Ser Glu Ser Lys Met Glu
            585                 590                 595 gat gga aga ctt gta gtc ggt tgg caa cct acg gga tat aag tta aat       1939
Asp Gly Arg Leu Val Val Gly Trp Gln Pro Thr Gly Tyr Lys Leu Asn
            600                 605                 610 cct gag aag caa ggg gct cta gtt ttg aat aat ctc tgg agt cat tat       1987
Pro Glu Lys Gln Gly Ala Leu Val Leu Asn Asn Leu Trp Ser His Tyr
            615                 620                 625 aca gat ctt aga gct ctt aag cag gag atc ttt gct cat cat acg ata       2035
Thr Asp Leu Arg Ala Leu Lys Gln Glu Ile Phe Ala His His Thr Ile
630                 635                 640                 645 gct caa aga atg gag tta gat ttc tcg aca aat gtc tgg gga tca gga       2083
Ala Gln Arg Met Glu Leu Asp Phe Ser Thr Asn Val Trp Gly Ser Gly
            650                 655                 660 tta ggt gtt gtt gaa gat tgt cag aac atc gga gag ttt gat ggg ttc       2131
Leu Gly Val Val Glu Asp Cys Gln Asn Ile Gly Glu Phe Asp Gly Phe
            665                 670                 675 aaa cat cat ctc aca ggg tat gcc cta ggc ttg gat aca caa cta gtt       2179
Lys His His Leu Thr Gly Tyr Ala Leu Gly Leu Asp Thr Gln Leu Val
            680                 685                 690 gaa gac ttc tta att gga gga tgt ttc tca cag ttc ttt ggt aaa act       2227
Glu Asp Phe Leu Ile Gly Gly Cys Phe Ser Gln Phe Phe Gly Lys Thr
            695                 700                 705 gaa agc caa tcc tac aaa gct aag aac gat gtg aag agt tat atg gga       2275
Glu Ser Gln Ser Tyr Lys Ala Lys Asn Asp Val Lys Ser Tyr Met Gly
710                 715                 720                 725 gct gct tat gcg ggg att tta gca ggt cct tgg tta ata aaa gga gct       2323
Ala Ala Tyr Ala Gly Ile Leu Ala Gly Pro Trp Leu Ile Lys Gly Ala
            730                 735                 740 ttt gtt tac ggt aat ata aac aac gat ttg act aca gat tac ggt act       2371
```

```
                Phe Val Tyr Gly Asn Ile Asn Asn Asp Leu Thr Thr Asp Tyr Gly Thr
                            745                 750                 755 tta ggt att tca aca ggt tca tgg ata gga aaa ggg ttt atc gca ggc          2419
Leu Gly Ile Ser Thr Gly Ser Trp Ile Gly Lys Gly Phe Ile Ala Gly
        760                 765                 770 aca agc att gat tac cgc tat att gta aat cct cga cgg ttt ata tcg          2467
Thr Ser Ile Asp Tyr Arg Tyr Ile Val Asn Pro Arg Arg Phe Ile Ser
775                 780                 785 gca atc gta tcc aca gtg gtt cct ttt gta gaa gcc gag tat gtc cgt          2515
Ala Ile Val Ser Thr Val Val Pro Phe Val Glu Ala Glu Tyr Val Arg
790                 795                 800                 805 ata gat ctt cca gaa att agc gaa cag ggt aaa gag gtt aga acg ttc          2563
Ile Asp Leu Pro Glu Ile Ser Glu Gln Gly Lys Glu Val Arg Thr Phe
                810                 815                 820 caa aaa act cgt ttt gag aat gtc gcc att cct ttt gga ttt gct tta          2611
Gln Lys Thr Arg Phe Glu Asn Val Ala Ile Pro Phe Gly Phe Ala Leu
            825                 830                 835 gaa cat gct tat tcg cgt ggc tca cgt gct gaa gtg aac agt gta cag          2659
Glu His Ala Tyr Ser Arg Gly Ser Arg Ala Glu Val Asn Ser Val Gln
        840                 845                 850 ctt gct tac gtc ttt gat gta tat cgt aag gga cct gtc tct ttg att          2707
Leu Ala Tyr Val Phe Asp Val Tyr Arg Lys Gly Pro Val Ser Leu Ile
    855                 860                 865 aca ctc aag gat gct gct tat tct tgg aag agt tat ggg gta gat att          2755
Thr Leu Lys Asp Ala Ala Tyr Ser Trp Lys Ser Tyr Gly Val Asp Ile
870                 875                 880                 885 cct tgt aaa gct tgg aag gct cgc ttg agc aat aat acg gaa tgg aat          2803
Pro Cys Lys Ala Trp Lys Ala Arg Leu Ser Asn Asn Thr Glu Trp Asn
                890                 895                 900 tca tat tta agt acg tat tta gcg ttt aat tat gaa tgg aga gaa gat          2851
Ser Tyr Leu Ser Thr Tyr Leu Ala Phe Asn Tyr Glu Trp Arg Glu Asp
            905                 910                 915 ctg ata gct tat gac ttc aat ggt ggt atc cgt att att ttc                  2893
Leu Ile Ala Tyr Asp Phe Asn Gly Gly Ile Arg Ile Ile Phe
        920                 925                 930 tagttcgatg tgacagggct tcaatcaaaa aaaagggtta cttttagtaa ccctttttta        2953
tttctcttaa tgcttatagt tcgatgatct ttaatacata gagcaagtag gcgatacaag        3013
ctttattagg ttcataggtc tctgggtcca ttaagag                                 3050

<210> SEQ ID NO 2
<211> LENGTH: 931
<212> TYPE: PRT
<213> ORGANISM: Chlamydia pneumoniae

<400> SEQUENCE: 2

Met Leu Glu Glu His Pro Val Val Ser Ser Thr Asp Ile Arg Gly Gly
 1               5                  10                  15

Gly Ala Ile Leu Ala Gln His Ile Phe Ile Thr Asp Asn Thr Gly Asn
                20                  25                  30

Leu Arg Phe Ser Gly Asn Leu Gly Gly Gly Glu Glu Ser Ser Thr Val
            35                  40                  45

Gly Asp Leu Ala Ile Val Gly Gly Ala Leu Leu Ser Thr Asn Glu
        50                  55                  60

Val Asn Val Cys Ser Asn Gln Asn Val Val Phe Ser Asp Asn Val Thr
 65                  70                  75                  80

Ser Asn Gly Cys Asp Ser Gly Gly Ala Ile Leu Ala Lys Lys Val Asp
                85                  90                  95
```

-continued

```
Ile Ser Ala Asn His Ser Val Glu Phe Val Ser Asn Gly Ser Gly Lys
            100                 105                 110
Phe Gly Gly Ala Val Cys Ala Leu Asn Glu Ser Val Asn Ile Thr Asp
        115                 120                 125
Asn Gly Ser Ala Val Ser Phe Ser Lys Asn Arg Thr Arg Leu Gly Gly
    130                 135                 140
Ala Gly Val Ala Ala Pro Gln Gly Ser Val Thr Ile Cys Gly Asn Gln
145                 150                 155                 160
Gly Asn Ile Ala Phe Lys Glu Asn Phe Val Phe Gly Ser Glu Asn Gln
                165                 170                 175
Arg Ser Gly Gly Gly Ala Ile Ile Ala Asn Ser Ser Val Asn Ile Gln
            180                 185                 190
Asp Asn Ala Gly Asp Ile Leu Phe Val Ser Asn Ser Thr Gly Ser Tyr
        195                 200                 205
Gly Gly Ala Ile Phe Val Gly Ser Leu Val Ala Ser Glu Gly Ser Asn
    210                 215                 220
Pro Arg Thr Leu Thr Ile Thr Gly Asn Ser Gly Asp Ile Leu Phe Ala
225                 230                 235                 240
Lys Asn Ser Thr Gln Thr Ala Ala Ser Leu Ser Glu Lys Asp Ser Phe
                245                 250                 255
Gly Gly Gly Ala Ile Tyr Thr Gln Asn Leu Lys Ile Val Lys Asn Ala
            260                 265                 270
Gly Asn Val Ser Phe Tyr Gly Asn Arg Ala Pro Ser Gly Ala Gly Val
        275                 280                 285
Gln Ile Ala Asp Gly Gly Thr Val Cys Leu Glu Ala Phe Gly Gly Asp
    290                 295                 300
Ile Leu Phe Glu Gly Asn Ile Asn Phe Asp Gly Ser Phe Asn Ala Ile
305                 310                 315                 320
His Leu Cys Gly Asn Asp Ser Lys Ile Val Glu Leu Ser Ala Val Gln
                325                 330                 335
Asp Lys Asn Ile Ile Phe Gln Asp Ala Ile Thr Tyr Glu Glu Asn Thr
            340                 345                 350
Ile Arg Gly Leu Pro Asp Lys Asp Val Ser Pro Leu Ser Ala Pro Ser
        355                 360                 365
Leu Ile Phe Asn Ser Lys Pro Gln Asp Ser Ala Gln His His Glu
    370                 375                 380
Gly Thr Ile Arg Phe Ser Arg Gly Val Ser Lys Ile Pro Gln Ile Ala
385                 390                 395                 400
Ala Ile Gln Glu Gly Thr Leu Ala Leu Ser Gln Asn Ala Glu Leu Trp
                405                 410                 415
Leu Ala Gly Leu Lys Gln Glu Thr Gly Ser Ser Ile Val Leu Ser Ala
            420                 425                 430
Gly Ser Ile Leu Arg Ile Phe Asp Ser Gln Val Asp Ser Ser Ala Pro
        435                 440                 445
Leu Pro Thr Glu Asn Lys Glu Glu Thr Leu Val Ser Ala Gly Val Gln
    450                 455                 460
Ile Asn Met Ser Ser Pro Thr Pro Asn Lys Asp Lys Ala Val Asp Thr
465                 470                 475                 480
Pro Val Leu Ala Asp Ile Ile Ser Ile Thr Val Asp Leu Ser Ser Phe
                485                 490                 495
Val Pro Glu Gln Asp Gly Thr Leu Pro Leu Pro Pro Glu Ile Ile Ile
            500                 505                 510
Pro Lys Gly Thr Lys Leu His Ser Asn Ala Ile Asp Leu Lys Ile Ile
```

-continued

```
            515                 520                 525
Asp Pro Thr Asn Val Gly Tyr Glu Asn His Ala Leu Leu Ser Ser His
        530                 535                 540

Lys Asp Ile Pro Leu Ile Ser Leu Lys Thr Ala Glu Gly Met Thr Gly
545                 550                 555                 560

Thr Pro Thr Ala Asp Ala Ser Leu Ser Asn Ile Lys Ile Asp Val Ser
                565                 570                 575

Leu Pro Ser Ile Thr Pro Ala Thr Tyr Gly His Thr Gly Val Trp Ser
                580                 585                 590

Glu Ser Lys Met Glu Asp Gly Arg Leu Val Val Gly Trp Gln Pro Thr
        595                 600                 605

Gly Tyr Lys Leu Asn Pro Glu Lys Gln Gly Ala Leu Val Leu Asn Asn
610                 615                 620

Leu Trp Ser His Tyr Thr Asp Leu Arg Ala Leu Lys Gln Glu Ile Phe
625                 630                 635                 640

Ala His His Thr Ile Ala Gln Arg Met Glu Leu Asp Phe Ser Thr Asn
                645                 650                 655

Val Trp Gly Ser Gly Leu Gly Val Val Glu Asp Cys Gln Asn Ile Gly
            660                 665                 670

Glu Phe Asp Gly Phe Lys His His Leu Thr Gly Tyr Ala Leu Gly Leu
        675                 680                 685

Asp Thr Gln Leu Val Glu Asp Phe Leu Ile Gly Gly Cys Phe Ser Gln
    690                 695                 700

Phe Phe Gly Lys Thr Glu Ser Gln Ser Tyr Lys Ala Lys Asn Asp Val
705                 710                 715                 720

Lys Ser Tyr Met Gly Ala Ala Tyr Ala Gly Ile Leu Ala Gly Pro Trp
                725                 730                 735

Leu Ile Lys Gly Ala Phe Val Tyr Gly Asn Ile Asn Asn Asp Leu Thr
            740                 745                 750

Thr Asp Tyr Gly Thr Leu Gly Ile Ser Thr Gly Ser Trp Ile Gly Lys
        755                 760                 765

Gly Phe Ile Ala Gly Thr Ser Ile Asp Tyr Arg Tyr Ile Val Asn Pro
    770                 775                 780

Arg Arg Phe Ile Ser Ala Ile Val Ser Thr Val Val Pro Phe Val Glu
785                 790                 795                 800

Ala Glu Tyr Val Arg Ile Asp Leu Pro Glu Ile Ser Glu Gln Gly Lys
                805                 810                 815

Glu Val Arg Thr Phe Gln Lys Thr Arg Phe Glu Asn Val Ala Ile Pro
            820                 825                 830

Phe Gly Phe Ala Leu Glu His Ala Tyr Ser Arg Gly Ser Arg Ala Glu
        835                 840                 845

Val Asn Ser Val Gln Leu Ala Tyr Val Phe Asp Val Tyr Arg Lys Gly
850                 855                 860

Pro Val Ser Leu Ile Thr Leu Lys Asp Ala Ala Tyr Ser Trp Lys Ser
865                 870                 875                 880

Tyr Gly Val Asp Ile Pro Cys Lys Ala Trp Lys Ala Arg Leu Ser Asn
                885                 890                 895

Asn Thr Glu Trp Asn Ser Tyr Leu Ser Thr Tyr Leu Ala Phe Asn Tyr
            900                 905                 910

Glu Trp Arg Glu Asp Leu Ile Ala Tyr Asp Phe Asn Gly Gly Ile Arg
        915                 920                 925

Ile Ile Phe
    930
```

-continued

```
<210> SEQ ID NO 3
<211> LENGTH: 42
<212> TYPE: DNA
<213> ORGANISM: Chlamydia pneumoniae

<400> SEQUENCE: 3
ataagaatgc ggccgccacc atgttagaag aacatcctgt tg                  42

<210> SEQ ID NO 4
<211> LENGTH: 31
<212> TYPE: DNA
<213> ORGANISM: Chlamydia pneumoniae

<400> SEQUENCE: 4
cggggtaccg gaaaataata cggataccac c                              31
```